US007645593B2

(12) United States Patent
Dertinger et al.

(10) Patent No.: US 7,645,593 B2
(45) Date of Patent: Jan. 12, 2010

(54) KIT FOR ENUMERATING MAMMALIAN CELL MICRONUCLEI

(75) Inventors: Stephen D. Dertinger, Webster, NY (US); Sian E. Cairns, Clifton Park, NY (US); Svetlana L. Avlasevich, Webster, NY (US); Dorothea K. Torous, Rochester, NY (US)

(73) Assignee: Litron Laboratories, Ltd., Rochester, NY (US)

( * ) Notice: Subject to any disclaimer, the term of this patent is extended or adjusted under 35 U.S.C. 154(b) by 0 days.

(21) Appl. No.: 12/244,179

(22) Filed: Oct. 2, 2008

(65) Prior Publication Data

US 2009/0029386 A1 Jan. 29, 2009

Related U.S. Application Data

(62) Division of application No. 11/166,433, filed on Jun. 24, 2005, now Pat. No. 7,445,910.

(60) Provisional application No. 60/584,555, filed on Jul. 1, 2004.

(51) Int. Cl.
*C12Q 1/02* (2006.01)
*G01N 1/30* (2006.01)
*G01N 33/48* (2006.01)

(52) U.S. Cl. .................. 435/29; 435/40.5; 435/259

(58) Field of Classification Search .................. None
See application file for complete search history.

(56) References Cited

U.S. PATENT DOCUMENTS

| 5,314,805 A | 5/1994 | Haugland et al. |
| 5,858,667 A | 1/1999 | Dertinger et al. |
| 6,100,038 A | 8/2000 | Dertinger et al. |

OTHER PUBLICATIONS

Applicant Declaration filed Apr. 18, 2008, for U.S. Appl. No. 11/166,433, pp. 1-8.*
OECD Guideline for the Testing of Chemicals, "Draft Proposal for a New Guideline 487: In Vitro Micronucleus Test," Jun. 2004.
Albertini et al., "Detailed Data on In Vitro MNT and In Vitro CA: Industrial Experience," Mutat. Res. 392:187-208 (1997).
Böcker et al., "Image Processing Algorithms for the Automated Micronucleus Assay in Binucleated Human Lymphocytes," Cytometry 19:283-294 (1995).
Bonassi et al., "Human Population Studies with Cytogenetic Biomarkers: Review of the Literature and Future Prospectives," Environ. Molec. Mutagen. 45:258-270 (2005).
Brando et al., "Cytofluorometric Methods for Assessing Absolute Numbers of Cell Subsets in Blood," Cytometry 42:327-346 (2000).
Darzynkiewicz et al., "Cytometry in Cell Necrobiology: Analysis of Apoptosis and Accidental Cell Death (Necrosis)," Cytometry 27:1-20 (1997).
Garriott et al., "A Protocol for the In Vitro Micronucleus Test. I. Contributions to the Development of a Protocol Suitable for Regulatory Submissions from an Examination of 16 Chemicals with Different Mechanisms of Action and Different Levels of Activity," Mutat. Res. 517:123-134 (2002).
Hayashi et al., "An Application of Acridine Orange Fluorescent Staining to the Micronucleus Test," Mutat. Res. 120:241-247 (1983).
Hayashi et al., "In Vivo Rodent Erythrocyte Micronucleus Assay. II. Some Aspects of Protocol Design Including Repeated Treatments, Integration With Toxicity Testing, and Automated Scoring," Environ. Mol. Mutagen. 35:234-252 (2000).
Heddle, "A Rapid In Vivo Test for Chromosome Damage," Mutat. Res. 18:187-190 (1973).
Idziorek et al., "YOPRO-1 Permits Cytofluorometric Analysis of Programmed Cell Death (Apoptosis) Without Interfering With Cell Viability," J. Immunological Methods 185:249-258 (1995).
Kirsch-Volders et al., "Report from the In Vitro Micronucleus Assay Working Group," Mutat. Res. 540:153-163 (2003).
Matsuoka et al., "Evaluation of the Micronucleus Test Using a Chinese Hamster Cell Line as an Alternative to the Conventional In Vitro Chromosomal Aberration Test," Mutat. Res. 272:223-236 (1993).
Matsushima et al., "Validation Study of the In Vitro Micronucleus Test in a Chinese Hamster Lung Cell Line (CHL/IU)," Mutagenesis 14:569-580 (1999).
Miller et al., "Comparative Evaluation of the In Vitro Micronucleus Test and the In Vitro Chromosome Aberration Test: Industrial Experience," Mutat. Res. 392:45-59 (1997).
Miller et al., "Evaluation of the In Vitro Micronucleus Test as an Alternative to the In Vitro Chromosome Aberration Assay: Position of the GUM Working Group on the In Vitro Micronucleus Test," Mutat. Res. 410:81-116 (1998).
Nesslany et al., "A Micromethod for the In Vitro Micronucleus Assay," Mutagenesis 14: 403-410 (1999).
Nüsse et al., "Factors Influencing the DNA Content of Radiation-Induced Micronuclei," Int. J. Radiat. Biol. 62:587-602 (1992).
Nüsse et al., "Flow Cytometric Analysis of Micronuclei Found in Cells After Irradiation," Cytometry 5:20-25 (1984).
Nüsse et al., "Flow Cytometric Analysis of Micronuclei In Cell Cultures and Human Lymphocytes: Advantages and Disadvantages," Mutat. Res. 392:109-115 (1997).
Phelps et al., "A Protocol for the In Vitro Micronucleus Test. II. Contribution to the Validation of a Protocol Suitable for Regulatory Submissions from an Examination of 10 Chemicals with Different Mechanisms of Action and Different Levels of Activity," Mutat. Res. 521:103-112 (2002).
Riedy et al., "Use of a Photolabeling Technique to Identify Nonviable Cells in Fixed Homologous or Heterologous Cell Populations," Cytometry 12:133-139 (1991).

(Continued)

*Primary Examiner*—David M Naff
(74) *Attorney, Agent, or Firm*—Nixon Peabody LLP

(57) ABSTRACT

The present invention relates a method for the enumeration of mammalian cell micronuclei, while distinguishing micronuclei from the chromatin of dead and dying cells. The method utilizes differential staining of chromatin from dead and dying cells, to distinguish the chromatin from micronuclei and nuclei that can be detected based upon fluorescent emission and light scatter following exposure to an excitatory light source. Counting of micronuclei events relative to the number of nuclei can be used to assess the DNA-damaging potential of a chemical agent, the DNA-damaging potential of a physical agent, the effects of an agent which can modify endogenously-induced DNA damage, and the effects of an agent which can modify exogenously-induced DNA damage. Kits for practicing the invention are also disclosed.

17 Claims, 20 Drawing Sheets

OTHER PUBLICATIONS

Roman et al., "Evaluation of a New Procedure for the Flow Cytometric Analysis of In Vitro, Chemically Induced Micronuclei in V79 Cells," Environ. Molec. Mutagen. 32:387-396 (1998).

Schmid, "The Micronucleus Test," Mutat. Res. 31:9-15 (1975).

Schreiber et al., "An Automated Flow Cytometic Micronucleus Assay for Human Lymphocytes," Int. J. Radiat. Biol. 62:695-709 (1992).

Schreiber et al., "Multiparametric Flow Cytometric Analysis of Radiation-Induced Micronuclei in Mammalian Cell Cultures," Cytometry 13:90-102 (1992).

Verhaegen et al., "Scoring of Radiation-Induced Micronuclei in Cytokineses-Blocked Human Lymphocytes by Automated Image Analysis," Cytometry 17:119-127 (1994).

Vermes et al., "A Novel Assay for Apoptosis. Flow Cytometric Detection of Phosphatidylserine Expression on Early Apoptotic Cells Using Fluorescein Labelled Annexin V," J. Immunol. Meth. 184:39-51 (1995).

Viaggi et al., "Flow Cytometric Analysis of Micronuclei in the CD2'/- Subpopulation of Human Lymphocytes Enriched by Magnetic Separation," Int. J. Radiat. Biol. 67:193-202 (1995).

Von der Hude et al., "In Vitro Micronucleus Assay with Chinese Hamster V79 Cells—Results of a Collaborative Study with In Situ Exposure to 26 Chemical Substances," Mutat. Res. 468:137-163 (2000).

Vral et al., "The In Vitro CytoKinesis-Block Micronucleus Assay: A Detailed Description of an Improved Slide Preparation Technique for the Automated Detection of Micronuclei in Human Lymphocytes," Mutagenesis 9:439-443 (1994).

Wessels et al., "Flow Cytometric Detection of Micronuclei by Combined Staining of DNA and Membranes," Cytometry 19:201-208 (1995).

Zhan et al., "Genotoxicity of Microcystin-LR in Human Lymphoblastoid TK6 Cells," Mutat. Res. 557:1-6 (2004).

* cited by examiner

KIT FOR ENUMERATING MAMMALIAN CELL MICRONUCLEI

This application is a divisional of U.S. patent application Ser. No. 11/166,433 filed Jun. 24, 2005, now U.S. Pat. No. 7,445,910, which claims priority benefit of U.S. Provisional Patent Application Ser. No. 60/584,555 filed Jul. 1, 2004, the entire disclosure of which is hereby incorporated by reference in its entirety.

The present invention was made with funding received from the National Cancer Institute under grants R43CA094493 and R44CA094493. The U.S. government has certain rights in this invention.

BACKGROUND OF THE INVENTION

The induction of DNA damage and the resulting sequelae of mutations and chromosomal rearrangements are primary mechanisms by which cancers arise. These types of events have also been implicated in diseases such as atherosclerosis, processes such as aging, and the development of birth defects such as Down syndrome. Therefore, there is an important need for sensitive methods which are capable of identifying chemical or physical agents that can alter DNA. Given the tremendous cost of long-term chronic studies such as 2-year carcinogenicity tests, short- and medium-term systems for predicting DNA damage potential continue play a vital role in tumorigenic agent identification. In fact, the need for short-term tests that have a high throughput capacity has never been greater. Advances in molecular biology and combinatorial chemistry have provided large numbers of potential targets and many novel compounds that may be useful for treating or preventing disease. However, before such agents can be tested and widely administered, acceptable toxicity to critical organs must be demonstrated. In the area of environmental health and safety, many natural and industrially manufactured compounds and formulations have not been adequately evaluated for toxicity. In both arenas, traditional toxicity evaluations are labor intensive and require extensive use of in vivo assays. This situation offers opportunities for methods that are able to quickly and inexpensively determine toxicological profiles of potential therapeutic drugs and environmental agents.

Micronuclei are formed upon cell division in cells with DNA double-strand break(s) or dysfunctional mitotic spindle apparatus. Based on this detailed understanding of micronuclei origin, the rodent-based micronucleus test has become the most widely utilized in vivo system for evaluating the clastogenic and aneugenic potential of chemicals (Heddle, "A Rapid In Vivo Test for Chromosome Damage," *Mutat. Res.* 18:187-190 (1973); Schmid, "The Micronucleus Test," *Mutat. Res.* 31:9-15 (1975); Hayashi et al., "In Vivo Rodent Erythrocyte Micronucleus Assay. II. Some Aspects of Protocol Design Including Repeated Treatments, Integration With Toxicity Testing, and Automated Scoring," *Environ. Mol. Mutagen.* 35:234-252 (2000)). These rodent-based tests are most typically performed as erythrocyte-based assays. Since erythroblast precursors are a rapidly dividing cell population, and their nucleus is expelled a few hours after the last mitosis, micronucleus-associated chromatin is particularly simple to detect in reticulocytes and normochromatic erythrocytes given appropriate staining (e.g., acridine orange) (Hayashi et al., "An Application of Acridine Orange Fluorescent Staining to the Micronucleus Test," *Mutat. Res.* 120:241-247 (1983)).

One of the short-term test systems that is believed to hold great promise as a rapid tool for screening drug candidates and other chemicals for genotoxic activity is the in vitro micronucleus test. Analogous to the way in vivo erythrocyte-based micronucleus tests have become more common than in vivo chromosome aberration analyses, a growing consensus has been forming that in vitro micronucleus assays could largely replace in vitro chromosome aberration studies. While both endpoints are capable of detecting agents that cause structural or numerical chromosome aberrations, in vitro micronucleus formation is technically easier to perform and score. The difficulty, however, is identifying the procedures that can reliably achieve an in vitro micronucleus assay that can satisfy the need for both fast and accurate results.

The in vitro micronucleus test demonstrates high concordance with chromosome aberration analyses, but it is executed more rapidly and requires less technical expertise (Matsuoka et al., "Evaluation of the Micronucleus Test Using a Chinese Hamster Cell Line as an Alternative to the Conventional In Vitro Chromosomal Aberration Test," *Mutat. Res.* 272:223-236 (1993); Miller et al., "Comparative Evaluation of the In Vitro Micronucleus Test and the In Vitro Chromosome Aberration Test: Industrial Experience," *Mutat. Res.* 392:45-59 (1997); Miller et al., "Evaluation of the In Vitro Micronucleus Test as an Alternative to the In Vitro Chromosome Aberration Assay: Position of the GUM Working Group on the In Vitro Micronucleus Test," *Mutat. Res.* 410:81-116 (1998)). These characteristics have led to its widespread use as an efficient and relatively simple method to screen drug candidates and other test articles for clastogenic and aneugenic potential (Nesslany et al., "A Micromethod for the In Vitro Micronucleus Assay," *Mutagenesis* 14: 403-410 (1999)). Furthermore, there have been concerted efforts to establish robust protocols so that the in vitro micronucleus test can serve as a source of cytogenetic damage information for regulatory submission purposes in place of in vitro chromosome aberration results (Albertini et al., "Detailed Data on In Vitro MNT and In Vitro CA: Industrial Experience," *Mutat. Res.* 392:187-208 (1997); von der Hude et al., "In Vitro Micronucleus Assay with Chinese Hamster V79 Cells—Results of a Collaborative Study with In Situ Exposure to 26 Chemical Substances," *Mutat. Res.* 468:137-163 (2000); Garriott et al., "A Protocol for the In Vitro Micronucleus Test. I. Contributions to the Development of a Protocol Suitable for Regulatory Submissions from an Examination of 16 Chemicals with Different Mechanisms of Action and Different Levels of Activity," *Mutat. Res.* 517:123-134 (2002); Phelps et al., "A Protocol for the In Vitro Micronucleus Test. II. Contribution to the Validation of a Protocol Suitable for Regulatory Submissions from an Examination of 10 Chemicals with Different Mechanisms of Action and Different Levels of Activity," *Mutat. Res.* 521:103-112 (2002); Kirsch-Volders et al., "Report from the In Vitro Micronucleus Assay Working Group," *Mutat. Res.* 540:153-163 (2003)). In fact these activities have progressed to the point that draft guidelines have been written by the Organisation for Economic Co-operation and Development ("OECD") ("Draft Proposal for a New Guideline 487: In Vitro Micronucleus Test," June 2004).

Given the growing enthusiasm for the in vitro micronucleus endpoint, numerous efforts to automate the scoring phase of the technique have been described in the literature—methods based on image analysis, laser scanning cytometry, and flow cytometry have all been reported (Nüsse et al., "Flow Cytometric Analysis of Micronuclei Found in Cells After Irradiation," *Cytometry* 5:20-25 (1984); Schreiber et al., "An Automated Flow Cytometric Micronucleus Assay for Human Lymphocytes," *Int. J. Radiat. Biol.* 62:695-709 (1992); Schreiber et al., "Multiparametric Flow Cytometric Analysis of Radiation-Induced Micronuclei in Mammalian Cell Cultures," *Cytometry* 13:90-102 (1992); Vral et al., "The In Vitro CytoKinesis-Block Micronucleus Assay: A Detailed Description of an Improved Slide Preparation Technique for the Automated Detection of Micronuclei in Human Lymphocytes," *Mutagenesis* 9:439-443 (1994); Verhaegen et al., "Scoring of Radiation-Induced Micronuclei in Cytokineses-Blocked Human Lymphocytes by Automated Image Analysis," *Cytometry* 17:119-127 (1994); Bocker et al., "Image Processing Algorithms for the Automated Micronucleus Assay in Binucleated Human Lymphocytes," *Cytometry* 19:283-294 (1995); Wessels et al., "Flow cytometric Detection of Micronuclei by Combined Staining of DNA and Membranes," *Cytometry* 19:201-208 (1995); Viaggi et al., "Flow Cytometric Analysis of Micronuclei in the CD2+ Subpopulation of Human Lymphocytes Enriched by Magnetic Separation," *Int. J. Radiat. Biol.* 67:193-202 (1995); Nüsse et al., "Flow Cytometric Analysis of Micronuclei In Cell Cultures and Human Lymphocytes: Advantages and Disadvantages," *Mutat. Res.* 392:109-115 (1997); Roman et al., "Evaluation of a New Procedure for the Flow Cytometric Analysis of In Vitro, Chemically Induced Micronuclei in V79 Cells," *Environ. Molec. Mutagen.* 32:387-396 (1998)). The most established technique for high throughput in vitro micronuclei scoring, both in terms of years since original description and the number of peer-reviewed publications, is the flow cytometric ("FCM") procedure developed by Nüsse and colleagues (Nüsse et al., "Flow Cytometric Analysis of Micronuclei Found in Cells After Irradiation," Cytometry 5:20-25 (1984); Schreiber et al., "An Automated Flow Cytometic Micronucleus Assay for Human Lymphocytes," *Int. J. Radiat. Biol.* 62:695-709 (1992); Schreiber et al., "Multiparametric Flow Cytometric Analysis of Radiation-Induced Micronuclei in Mammalian Cell Cultures," *Cytometry* 13:90-102 (1992); Nüsse et al., "Flow Cytometric Analysis of Micronuclei in Cell Cultures and Human Lymphocytes Advantages and Disadvantages," *Mutat. Res.* 392:109-115 (1997)).

As the major limitation of FCM-based techniques has been their inability to distinguish true micronuclei from apoptotic bodies, methods for differential staining of micronuclei from the chromatin of dead and dying cells are needed.

The present invention overcomes the disadvantages of prior art approaches, and satisfies the need of establishing a robust, reliable, high throughput in vitro micronucleus assay.

SUMMARY OF THE INVENTION

A first aspect of the present invention relates to a method for the enumeration of mammalian cell micronuclei, while distinguishing micronuclei from the chromatin of dead and dying cells. This method involves contacting a sample containing mammalian cells with a first fluorescent DNA dye that permeates dead and dying cells but not viable cells, that covalently binds chromatin, and that has a fluorescence emission spectrum. The sample is contacted with one or more lysis solutions that result in digestion of mammalian cell outer membranes but retention of nuclear membranes, thereby forming free nuclei and/or micronuclei. The free nuclei and/or micronuclei are contacted with RNase to substantially degrade RNA. Cellular DNA is stained with a second fluorescent DNA dye having a fluorescent emission spectrum which does not substantially overlap with the fluorescent emission spectrum of the first fluorescent DNA dye. The first and second fluorescent DNA dyes are excited with light of appropriate excitation wavelength. The fluorescent emission and light scatter produced by the nuclei and/or micronuclei are detected, while chromatin from the dead and dying cells is excluded, and the number of micronuclei in the sample relative to the number of nuclei is counted.

A second aspect of the present invention relates to a method of assessing the DNA-damaging potential of a chemical or physical agent. This method involves exposing a sample containing mammalian cells to a chemical or physical agent and performing the method according to the first aspect of the present invention. A significant deviation in the frequency of micronuclei from a baseline micronuclei value in unexposed or vehicle control mammalian cells indicates the genotoxic potential of the chemical or physical agent.

A third aspect of the present invention relates to a method of evaluating the effects of an agent which can modify endogenously-induced DNA damage. This method of the present invention can be carried out by exposing mammalian cells to an agent that may modify endogenously-induced genetic damage to mammalian cells. The method according to the first aspect of the invention is performed with the exposed mammalian cells. A significant deviation in the frequency of micronuclei from a baseline micronuclei value in unexposed or vehicle-exposed mammalian cells indicates that the agent can modify endogenous DNA damage.

A fourth aspect of the present invention relates to a method of evaluating the effects of an agent which can modify exogenously-induced DNA damage. This method of the present invention can be carried out by exposing mammalian cells to an exogenous agent that causes genetic damage and an agent that may modify exogenously-induced genetic damage. The method according to the first aspect of the present invention is performed with the exposed mammalian cells. A significant deviation in the frequency of micronuclei from genotoxicant-exposed mammalian cells indicates that the agent can modify exogenously-induced DNA damage.

A fifth aspect of the present invention relates to a kit that includes: one or more mammalian cell membrane lysis solutions; a first fluorescent DNA dye that permeates the dead and dying cells, but not viable cells; a second fluorescent DNA dye having a fluorescent emission spectrum which does not substantially overlap with a fluorescent emission spectrum of the first fluorescent DNA dye; and RNase A solution.

A sixth aspect of the present invention relates to a method of assessing the cytotoxicity of a chemical or physical agent. This method involves exposing mammalian cells to a chemical or physical agent and performing the method according to the first aspect of the present invention. A significant deviation in the frequency of chromatin from dead and dying cells from a baseline value in unexposed or vehicle control mammalian cells indicates the cytotoxic potential of the chemical or physical agent.

A seventh aspect of the present invention relates to a method of assessing the effect of a chemical or physical agent on the cell-cycle of mammalian cells. This method involves exposing mammalian cells to a chemical or physical agent and performing the method according to the first aspect of the present invention. The detected nuclei are then displayed as a linear mode histogram. Dose-dependent perturbations are then detected, which indicate an adverse effect of the chemical or physical agent on the cell-cycle of mammalian cells.

The methods described herein provide for the enumeration of mammalian cell micronuclei using, preferably, flow cytometry technology. The primary advantage of this methodology relative to other flow cytometry-based procedures which have been reported to date is the use of a sequential staining procedure capable of differentially staining micronuclei and the chromatin of dead and dying cells, thus providing more accurate and reliable micronuclei measurements (see Nüsse et al., "Flow Cytometric Analysis of Micronuclei Found in Cells After Irradiation," *Cytometry* 5:20-25 (1984); Nüsse et al., "Factors Influencing the DNA Content of Radiation-Induced Micronuclei," Int. J. Radiat. Biol. 62:587-602 (1992); and Nüsse et al., "Flow Cytometric Analysis of Micronuclei in Cell Cultures and Human Lymphocytes Advantages and Disadvantages," Mutat. Res. 392:109-115 (1997), which are hereby incorporated by reference in their entirety). Thus, the present invention identifies procedures that can be employed for an automated in vitro micronucleus assay that can be used to evaluate agents (e.g., chemical or physical agents) for toxicity to mammalian cells. The procedure is fast, reliable, and accurate, and can be performed without the need for dosing of animals. Consequently, significant cost savings can be afforded by the present invention in the process of testing agents for geno- and/or cytotoxicity.

DETAILED DESCRIPTION OF THE INVENTION

Figure 1:
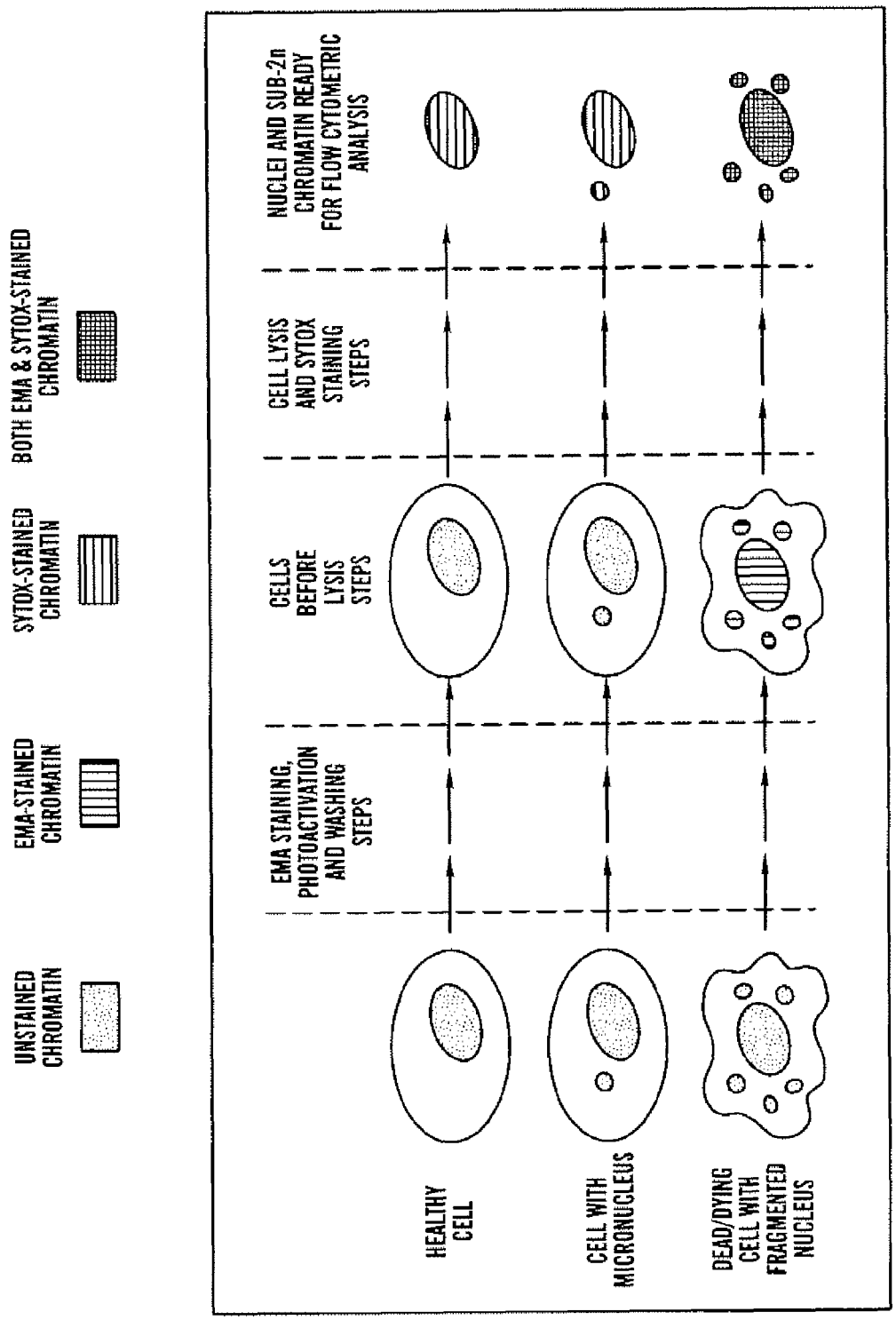
FIG. 1 is a schematic illustration of an exemplary cell staining technique according to the methods of the present invention. This two dye, sequential staining procedure enhances the reliability of flow cytometry-based analyses by differentially staining micronuclei and chromatin associated with dead and dying cells. Ethidium monoazide ("EMA") represents a preferred first DNA dye, and SYTOX represents a preferred second DNA dye.
Figure 2A:
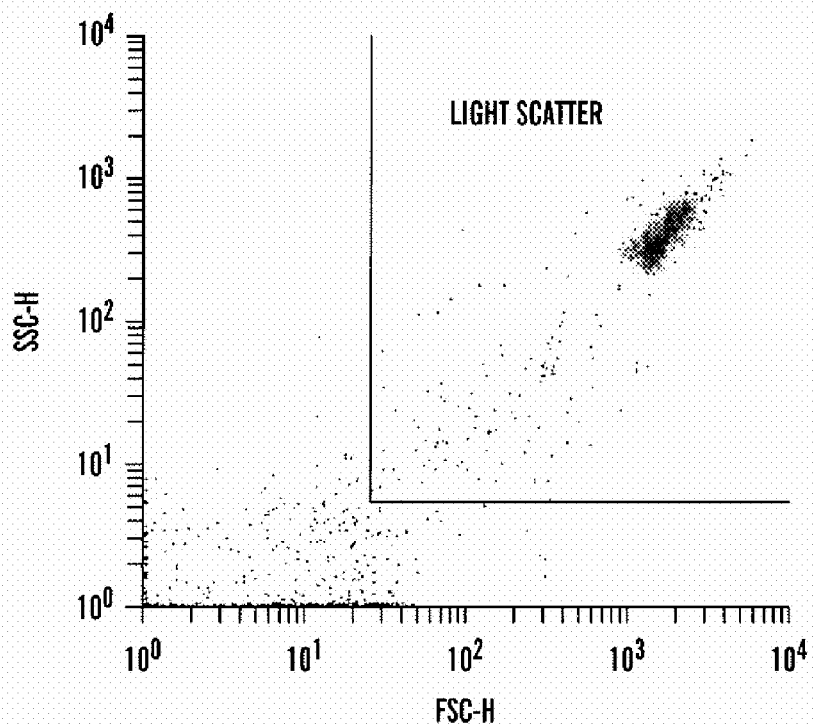
FIGS. 2A-H are histogram and bivariate plots of L5178Y cells treated with vehicle (FIGS. 2A-G) or 20 µg methyl methanesulfonate/ml (FIG. 2H). These graphs illustrate the gating strategy used to discriminate micronuclei from apoptotic chromatin and other spurious events. For events to be displayed and scored by FIGS. 2G and 2H, they needed to meet each of the following six criteria: within a side scatter versus forward scatter region (FIG. 2A); at least $1/100$ the SYTOX-associated fluorescence as G1 nuclei (FIG. 2B); within a region that excludes doublets (FIG. 2C); within a forward scatter versus SYTOX fluorescence region (FIG. 2D); within a side scatter versus SYTOX fluorescence region (FIG. 2E); and EMA-negative (FIG. 2F). The position of the micronucleus scoring region (MN) was designed to score events that exhibited $1/100$ to $1/10$ the SYTOX fluorescence intensity of G1 nuclei.
Figure 2B:
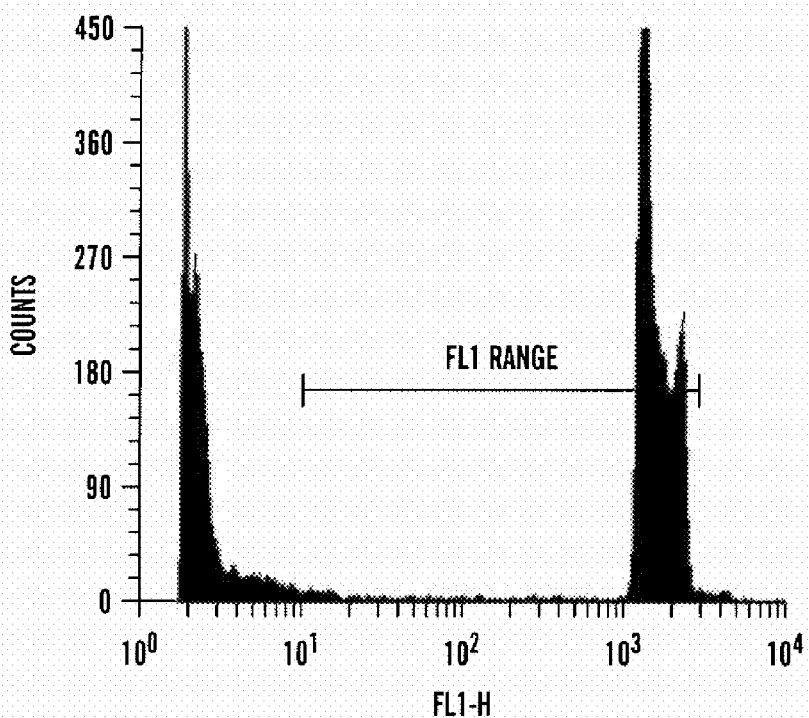
Figure 2C:
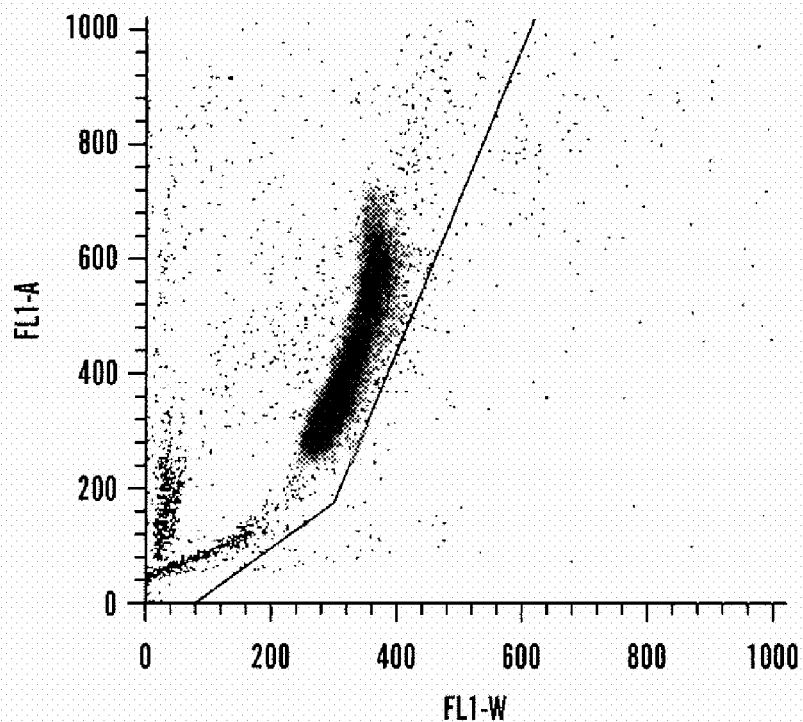
Figure 2D:
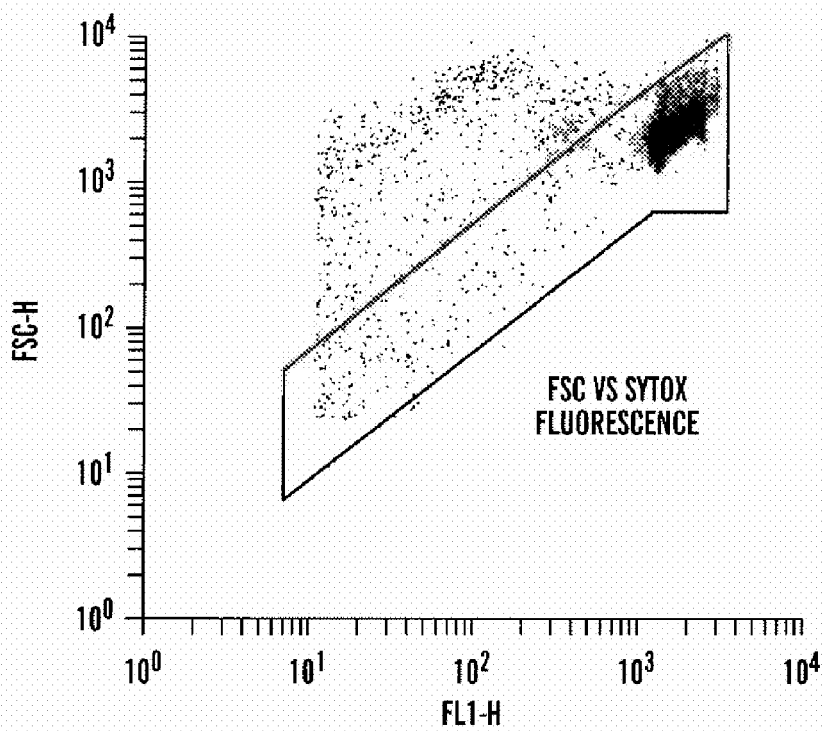
Figure 2E:
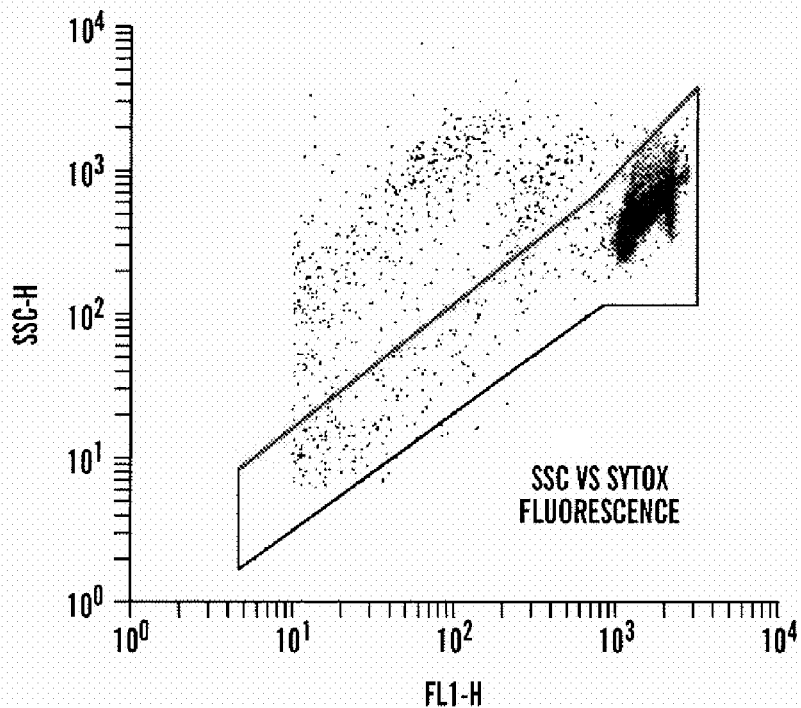
Figure 2F:
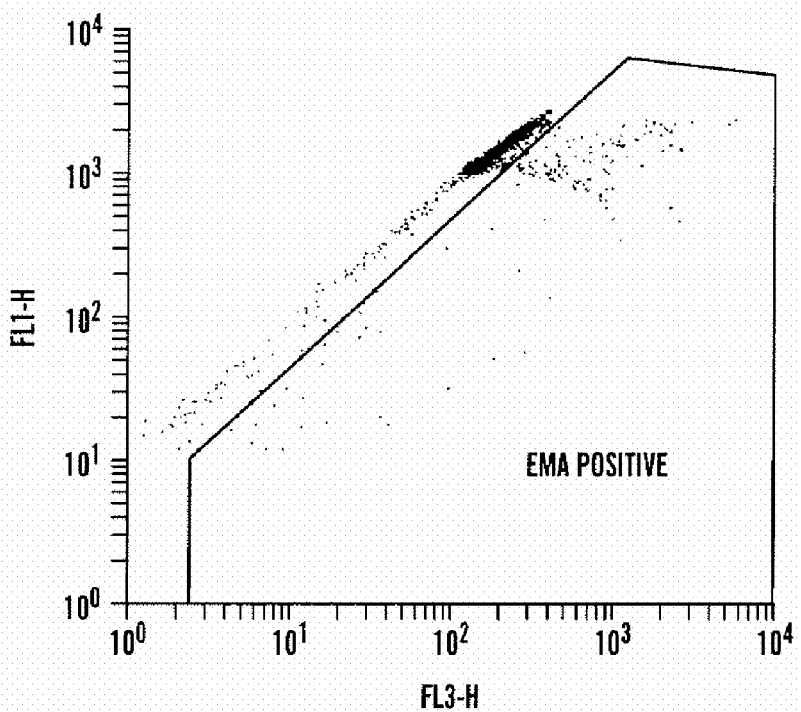
Figure 2G:
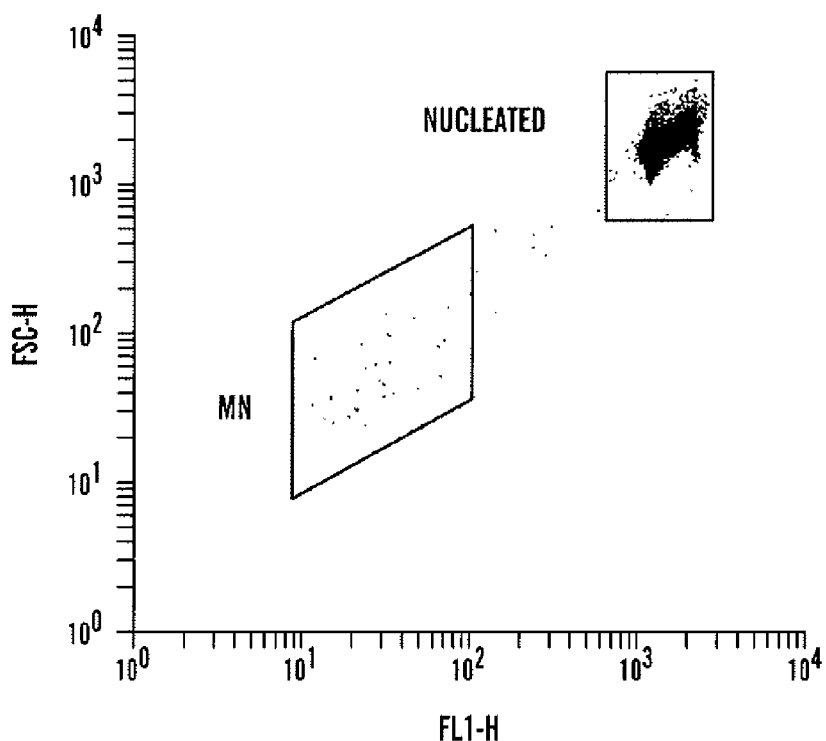
Figure 2H:
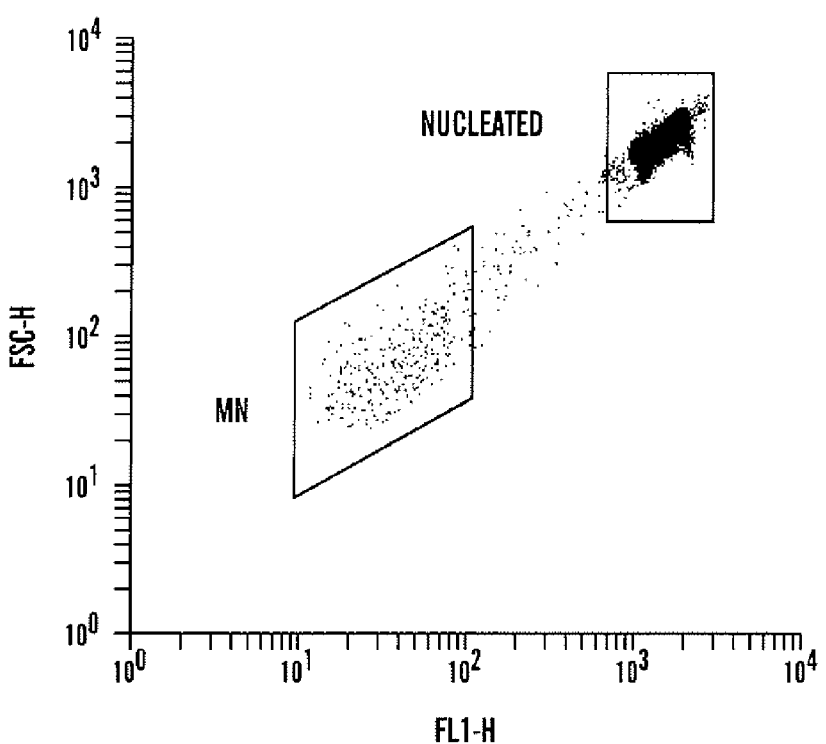

The present invention is directed to a method for the enumeration of micronuclei in mammalian cells using a standard, widely available flow cytometer apparatus which provides for excitation of fluorochromes and detection of resulting fluorescent emissions as well as light scatter signals.

A first aspect of the present invention relates to a method for the enumeration of mammalian cell micronuclei, while distinguishing micronuclei from the chromatin of dead and dying cells. This method involves contacting a sample containing mammalian cells with a first fluorescent DNA dye that permeates dead and dying cells but not viable cells, that covalently binds chromatin, and that has a fluorescence emission spectrum. The sample is contacted with one or more lysis solutions that result in digestion of mammalian cell outer membranes but retention of nuclear membranes, thereby forming free nuclei and/or micronuclei. The free nuclei and/or micronuclei are contacted with RNase to substantially degrade RNA. Cellular DNA is stained with a second fluorescent DNA dye having a fluorescent emission spectrum that does not substantially overlap with the fluorescent emission spectrum of the first fluorescent DNA dye. The first and second fluorescent DNA dyes are excited with light of appropriate excitation wavelength. The fluorescent emission and light scatter produced by the nuclei and/or micronuclei are detected, while chromatin from the dead and dying cells is excluded, and the number of micronuclei in the sample relative to the number of nuclei is counted.

Mammalian cells suitable for carrying out the methods of the present invention include, without limitation, immortalized cell lines, as well as cells which have only recently been harvested from mammalian species and placed into culture (i.e., primary cell cultures).

Preferred primary cell cultures are those that divide in culture (i.e., with appropriate growth media, which for some cell types requires the inclusion of cytokines and/or other factors such as mitogens). Exemplary cell types that can be screened easily using the methods of the present invention include, without limitation, blood lymphocytes, bone marrow-derived stem cells, hepatocytes, and keratinocytes.

Exemplary immortalized cell lines, include, without limitation, L5178Y cells, CHO (Matsuoka et al., "Evaluation of the Micronucleus Test Using a Chinese Hamster Cell Line as an Alternative to the Conventional In Vitro Chromosomal Aberration Test," *Mutat. Res.* 272:223-236 (1993); Garriott et al., "A Protocol for the In Vitro Micronucleus Test. I. Contributions to the Development of a Protocol Suitable for Regulatory Submissions form an Examination of 16 Chemicals with Different Mechanisms of Action and Different Levels of Activity," *Mutat. Res.* 517:123-134 (2002); Phelps et al., "A Protocol for the In Vitro Micronucleus Test. II. Contributions to the Validation of a Protocol Suitable for Regulatory Submissions from an Examination of 10 Chemicals with Different Mechanisms of Action and Different Levels of Activity," *Mutat. Res.* 521:103-112 (2002); which are hereby incorporated by reference in their entirety) V79 (von der Hude et al., "In Vitro Micronucleus Assay with Chinese Hamster V79 Cells—Results of a Collaborative Study with In Situ Exposure to 26 Chemical Substances," *Mutat. Res.* 468:137-163 (2000), which is hereby incorporated by reference in its entirety), and TK6 (Zhan et al., Genotoxicity of Microcystin-LR in Human Lymphoblastoid TK6 Cells," *Mutat. Res.* 557: 1-6 (2004), which is hereby incorporated by reference in its entirety). Each of these cell types is widely used in genotoxicity investigations. The characteristic that is most likely to define the compatibility of this scoring system with any particular cell line will be the kinetics by which apoptosing cells become permeable to the first dye. It is preferable that permeability occurs before nuclear fragmentation takes place in order to effectively exclude apoptotic bodies from the micronuclei scoring region. As noted in the Examples, cells that grow as a suspension culture (i.e., L5178Y) and cells that grow as an attachment culture (i.e., CHO-K1) have been used with success.

Micronuclei are membrane-bound, extra-nuclear, sub-2n DNA structures resulting from double-strand chromosome breaks or from the dysfunction of mitotic spindle apparatus. Micronuclei are also known as Howell-Jolly bodies in the hematology literature.

Chromatin of dead and dying cells is DNA derived from cells which are no longer viable, or from cells which have progressed to an irreversible stage of cell death. Thus, "dead and dying cells" is meant to encompass necrotic cell death typified by cytoplasmic swelling and rupture, as well as apoptotic cell death which is usually characterized by cellular and nuclear shrinkage, condensation of chromatin, and fragmentation of nuclei.

This first fluorescent DNA dye can be any such dye that can permeate the dead and dying cells, and then covalently bind chromatin. Preferably, the first fluorescent DNA dye is, at the time of contacting the cells in culture, in an inactive form. Thereafter, the dye is activated to a reactive form, which is controlled by conditions that can be easily manipulated in a laboratory setting (e.g., by light activation, change in pH, etc.). Upon activation, the dye should bind covalently to DNA, i.e., chromatin. When the dye is covalently bound to the DNA of dead and dying cells, it changes the nature of staining away from an equilibrium situation. In particular, this approach for staining ensures that the fluorescent signal that is imparted to dead and dying cells is not diminished during subsequent cell processing steps. In a preferred embodiment, the first fluorescent DNA dye is ethidium monoazide ("EMA"), which is efficiently converted to a reactive form through photoactivation.

The one or more lysis solutions can be any suitable lysis solution, or combination thereof, for cell membrane lysis. According to one embodiment, first and second lysis solutions are provided, with the first lysis solution having NaCl, Na-Citrate, and IPGAL in deionized water and the second lysis solution having citric acid and sucrose in deionized water. Cell lysis preferably occurs according to modifications to a procedure that has been described in the literature (Nüsse et al., "Flow Cytometric Analysis of Micronuclei Found in Cells After Irradiation," *Cytometry* 5:20-25 (1984); Nüsse et al., "Factors Influencing the DNA Content of Radiation-Induced Micronuclei," *Int. J. Radiat. Biol.* 62:587-602 (1992); and Nüsse et al., "Flow Cytometric Analysis of Micronuclei in Cell Cultures and Human Lymphocytes: Advantages and Disadvantages," *Mutat. Res.* 392:109-115 (1997), which are hereby incorporated by reference in their entirety).

In one embodiment of the methods of the present invention, contacting the sample with one or more lysis solutions and contacting the free nuclei and/or micronuclei with RNase may be carried out simultaneously. Alternatively, these steps are carried out sequentially.

In an another embodiment, contacting the sample with one or more lysis solutions, contacting the free nuclei and/or micronuclei with RNase, and staining cellular DNA with a second fluorescent DNA dye are carried out simultaneously. Alternatively, these steps are carried out sequentially.

Suitable second fluorescent DNA dyes are capable of staining cellular DNA at a concentration range detectable by flow cytometry, and have a fluorescent emission spectrum that does not substantially overlap with the fluorescent emission spectrum of the first fluorescent DNA dye. It should be appreciated by those of ordinary skill in the art that other nucleic acid dyes are known and are continually being identified. Any suitable nucleic acid dye with appropriate excitation and emission spectra can be employed, such as YO-PRO-1, SYTOX Green, SYBR Green I, SYTO11, SYTO12, SYTO13, BOBO, YOYO, and TOTO. A preferred second fluorescent DNA dye is SYTOX Green.

The first and second fluorescent DNA dyes have sufficiently distinct emission maxima. Preferably, the first and second fluorescent DNA dyes have similar excitation spectra. The advantage of similar excitation spectra is that it affords the use of the more widespread single-laser flow cytometer (as opposed to dual laser flow cyotometers). For example, when the first fluorescent DNA dye is EMA and the second fluorescent DNA dye is SYTOX Green, both the first and second fluorescent dyes are sufficiently excited by a flow cytometer equipped with a single 488 nm laser, while their different emission maxima can be detected by two separate detectors using standard filter sets (FIG. 1).

Single-laser flow cytometric analysis uses a single focused laser beam with an appropriate emission band to excite the first and second fluorescent DNA dyes. As stained nuclei, micronuclei, and chromatin debris pass through the focused laser beam, they exhibit a fluorescent emission maxima characteristic of the fluorescent dye(s) associated therewith. Dual- or multiple-laser flow cytometric analysis uses two or more focused laser beams with appropriate emission bands in much the same manner as described for the single-laser flow cytometer. Different emission bands afforded by the two or more lasers allow for additional combinations of nucleic acid dye(s) to be employed.

Preferably, the flow cytometer is equipped with appropriate detection devices to enable detection of the fluorescent emissions and light scatter produced by the nuclei, micronuclei, and chromatin debris. These "light scatter" signals serve as additional criteria which helps discriminate nuclei and micronuclei from apoptotic chromatin and other debris. The use of light scatter parameters to serve as additional criteria for accurately measuring micronuclei by flow cytometry has been described in the literature (Nüsse et al., "Flow Cytometric Analysis of Micronuclei in Cell Cultures and Human Lymphocytes: Advantages and Disadvantages," *Mutat. Res.* 392:109-115 (1997), which is hereby incorporated by reference in its entirety), which is demonstrated in conjunction with an ethidium monoazide-labeling criterion in the examples below.

A further aspect of the present invention relates to a method of assessing the DNA-damaging potential of a chemical or physical agent. This method involves exposing a sample containing mammalian cells to a chemical or physical agent and performing the method according to the first aspect of the present invention. A significant deviation in the frequency of micronuclei from a baseline micronuclei value in unexposed or vehicle control mammalian cells indicates the genotoxic potential of the chemical or physical agent.

Physical agents which are known to damage DNA include, without limitation, ionizing radiation, such as gamma and beta radiation, and UV radiation.

Chemical agents which are known to damage DNA include, without limitation, inorganic genotoxicants (e.g., arsenic, cadmium and nickel), organic genotoxicants (especially those used as antineoplastic drugs, such as cyclophosphamide, cisplatin, vinblastine, cytosine arabinoside, and others), anti-metabolites (especially those used as antineoplastic drugs, such as methotrexate and 5-fluorouracil), organic genotoxicants that are generated by combustion processes (e.g., polycyclic aromatic hydrocarbons such as benzo(a)pyrene), as well as organic genotoxicants that are found in nature (e.g., aflatoxins such as aflatoxin B1).

The methods of the present invention are suitable for assessing the DNA-damaging potential of both physical and chemical agents, either alone or in combination with other such agents. Agents which have known DNA-damaging potential and agents which are not known to have DNA-damaging potential or are presumed not to have DNA-damaging potential can be tested. In particular, physical and chemical agents which are under current investigation for therapeutic treatment, or agents which are being screened for potential therapeutic treatment are amenable to the methods of the present invention.

In carrying out the methods of the present invention, exposure of mammalian cells to physical or chemical agents is preferably carried out for a predetermined period of exposure time. Preferred exposure time for detecting chromosome breaking (i.e., clastogenic) agents is between about 3 and about 24 hours. There are some reports which suggest that a preferred exposure time for detecting aneugenic agents is approximately 24 hours (Phelps et al., "A Protocol for the In Vitro Micronucleus Test. II. Contributions to the Validation of a Protocol Suitable for Regulatory Submissions from an Examination of 10 Chemicals with Different Mechanisms of Action and Different Levels of Activity," *Mutat. Res.* 521: 103-112 (2002), which is hereby incorporated by reference in its entirety).

Methods of assessing the DNA-damaging potential of a physical or chemical agent may further involve a delay between the end of exposure and prior to performing cell harvest, staining, membrane lysis, and flow cytometric analysis according to the first aspect of the present invention. When employed, the delay or "recovery" period is preferably between about 5 minutes to about 24 hours, although longer or shorter delays can also be utilized.

To some degree, exposure time and recovery periods will be cell line- and chemical class-dependent. Persons of skill in the art can readily optimize the methods of the present invention for different cell lines and different physical or chemical agents.

Certain agents may offer protection from DNA damage, while others magnify risk of damage. The present invention can be used to evaluate the effects of an agent which can modify (i.e., enhance or suppress) such damage. To assess the suspected protective effects of an agent, it can be added to the culture of cells prior to, concurrently with, or soon after addition of a known genotoxicant. Any protective effect afforded by the agent can be measured relative to damage caused by the genotoxicant agent alone. For example, putative protective agents can be vitamins, bioflavonoids and antioxidants, dietary supplements (e.g., herbal supplements), or any other protective agent, naturally occurring or synthesized by man.

To assess the ability of an agent to synergistically or additively enhance genotoxicity, the agent can be added to the culture of cells prior to, concurrently with, or shortly after addition of a known genotoxicant. Any additive or synergistic effect caused by the agent can be measured relative to damage caused by the genotoxicant agent alone.

Concurrent cytotoxicity assessment of chemical and/or physical agents (with or without protective agents or enhancing agents) can also be made, pursuant to the methods of the present invention, such as (i) cell cycle effects based on the fluorescence intensity of the second fluorescent DNA dye which is exhibited by nuclei and (ii) cytotoxicity based on the percentage of particles that exhibit fluorescence associated with the first fluorescent DNA dye. The former can be achieved by assessing histograms to determine cell cycle progression of the cell population.

Thus, another aspect of the present invention relates to a method of assessing the cytotoxicity of a chemical or physical agent. This method involves exposing mammalian cells to a chemical or physical agent and performing the method according to the first aspect of the present invention. A significant deviation in the frequency of chromatin from dead and dying cells from a baseline value in unexposed or vehicle control mammalian cells indicates the cytotoxic potential of the chemical or physical agent.

A further aspect of the present invention relates to a method of assessing the effect of a chemical or physical agent on the cell-cycle of mammalian cells. This method involves exposing mammalian cells to a chemical or physical agent and performing the method according to the first aspect of the present invention. The detected nuclei are then displayed as a linear mode histogram. Dose-dependent perturbations are then detected, which indicate an adverse effect of the chemical or physical agent on the cell-cycle of mammalian cells.

Another aspect of the present invention relates to a method of evaluating the effects of an agent which can modify endogenously-induced DNA damage. This method of the present invention can be carried out by exposing mammalian cells to an agent that may modify endogenously-induced genetic damage to mammalian cells. The method according to the first aspect of the invention is then performed with the exposed mammalian cells. A significant deviation in the frequency of micronuclei from a baseline micronuclei value in unexposed or vehicle-exposed mammalian cells indicates that the agent can modify endogenous DNA damage.

A further aspect of the present invention relates to a method of evaluating the effects of an agent which can modify exogenously-induced DNA damage. This method of the present invention can be carried out by exposing mammalian cells to an exogenous agent that causes genetic damage and an agent that may modify exogenously-induced genetic damage. The method according to the first aspect of the present invention is then performed with the exposed mammalian cells. A significant deviation in the frequency of micronuclei from genotoxicant-exposed mammalian cells indicates that the agent can modify exogenously-induced DNA damage.

Yet another aspect of the present invention relates to a kit that includes: one or more mammalian cell membrane lysis solutions; first and second fluorescent DNA dyes as described above; and RNase A solution.

The kit may also include instructions that describe cell harvest and staining procedures and micronucleus scoring via flow cytometry. The kit may also include a computer readable storage medium that contains a cytometry data acquisition template for flow cytometric micronucleus scoring. A container having an in vitro culture of mammalian cells may also be included in the kit of the present invention.

The importance and utility of this in vitro micronuclei scoring system will be magnified considerably by miniaturization and process automation. Experiments described in the Examples, infra, were performed with relatively large volumes of cells, and $1.5 \times 10^6$ cells per measurement were processed for each flow cytometry analysis. This translates to high test article requirements and more culture medium, cells, etc., than is necessary to obtain reliable, repeatable results. For purposes of the present studies, the large number of cells facilitated parallel microscopy and several flow cytometry measurements per flask. This design helped to evaluate the reproducibility of cell handling, staining, and flow cytometry-analysis operations. However, significant reductions to numbers of cells and treatment volumes will allow for wide adoption of this or other techniques, especially in the context of lead prioritization and other early safety evaluation screening goals. Lysis solution volumes and/or dye concentrations can be adjusted and optimized for miniaturization.

Screening programs that wish to evaluate large numbers of chemicals will benefit from automation of processing steps. For instance, with flow cytometry, autoloaders (e.g., robotic equipment) are available which can operate in "walk-away" mode. Multi-well plates for sequential analysis of high volumes of work and other large-scale automation tools such as carousels are available to further automate the methods of the present invention. The processes described herein are expected to be fully compatible with such systems.

The degree to which micronuclei events in mitogen-stimulated lymphocytes can be more easily and rapidly scored relative to chromosome aberrations is in large part responsible for the cytokinesis-block micronuclei assay replacing chromosome aberration analyses as the cytogenetic damage endpoint of choice for human biomonitoring and epidemiological studies (Bonassi et al., "Human Population Studies with Cytogenetic Biomarkers: Review of the Literature and Future Prospectives," *Environ. Molec. Mutagen.* 45:258-270 (2005), which is hereby incorporated by reference in its entirety). Automation of the scoring phase of this process would supply additional impetus to utilize the micronuclei endpoint in human-based studies, perhaps encouraging its use in studies and on scales that are not traditionally viewed as compatible with this endpoint due to logistical and/or resource considerations.

EXAMPLES

The examples below are intended to exemplify the practice of the present invention but are by no means intended to limit the scope thereof.

Materials and Methods

Chemicals

The identities of the nine chemicals evaluated in the following examples, as well as solvent and other information, are listed in Table 1.

TABLE 1

Chemicals

| Chemical | Cas No. | Solvent | Genotoxic Mechanism |
| --- | --- | --- | --- |
| Methyl methanesulfonate | 66-27-3 | PBS | Alkylation |
| Hydroxyurea | 127-07-1 | Water | Ribonucleoside reductase inhibitor |
| Etoposide | 33419-42-0 | DMSO | Topoisomerase II inhibitor |
| Cyclophosphamide monohydrate | 6055-19-2 | Water | DNA cross-linker |
| Benzo[a]pyrene | 50-32-8 | DMSO | Diol epoxides, reactive O species |
| Vinblastine sulfate | 143-67-9 | DMSO | Mitotic spindle poison |
| Sucrose | 57-50-1 | RPMI + HS | Non-genotoxicant |
| Tributyltin methoxide | 1067-52-3 | Ethanol | Presumed non-genotoxicant |
| Dexamethasone | 50-02-2 | DMSO | Presumed non-genotoxicant |

PBS = phosphate buffered saline
RPMI + HS = growth medium
DMSO = dimethyl sulfoxide Each of these nine chemicals were purchased from Sigma-Aldrich Corp. (St. Louis, Mo.). Dimethyl sulfoxide (CAS No. 67-68-5), ethanol (CAS No. 64-17-5), DL-isocitric acid (CAS No. 1637-73-6), β-nicotinamide adenine dinucleotide phosphate sodium salt (CAS No. 1184-16-3), IGEPAL CA-630 (CAS No. 9036-19-5), propidium iodide (CAS No. 25535-16-4), fluorescein diacetate (CAS No. 596-09-8), acridine orange (CAS No. 65-61-2), sodium citrate (CAS No. 6132-04-3), citric acid (CAS No. 77-92-9), sucrose (CAS No. 57-50-1), and RNase A were also obtained from Sigma-Aldrich Corp. NaCl (CAS No. 7647-14-5) was purchased from J. T. Baker (Phillipsburg, N.J.). Annexin V-PE was obtained from the "Annexin V-PE Apoptosis Detection Kit I" (BD Pharmingen, La Jolla, Calif., cat no. 559763). The fluorescent dyes ethidium monoazide (cat. no. E11374), SYTOX Green (cat. no. S7020) and YO-PRO-1 iodide (cat. no. Y3603), were obtained from Molecular Probes, Eugene, Oreg.

Cells, Culture Medium, and Metabolic Activation

The L5178Y (tk+/−) and CHO-K1 cells used in these studies were from American Type Tissue Collection (ATCC) (Manassas, Va.). Cells were maintained in culture medium at 37° C., 5% $CO_2$, and in a humid atmosphere. Cells were maintained between approximately $1 \times 10^4$ and $1 \times 10^6$ cells/ml for routine passage.

For L5178Y cells, culture medium consisted of RPMI 1640 supplemented with 200 mM L-glutamine, 100 IU penicillin and 100 µg/ml streptomycin, to which heat inactivated horse serum was added for 10% v/v final concentration (all from MediaTech Inc., Herndon, Va.). Serum free medium was identical to culture medium but without 10% horse serum.

For CHO-K1 cells, culture medium consisted of HAM F-12 supplemented with 1.5 g/L sodium bicarbonate, 100 IU/ml penicillin and 100 µg/ml streptomycin, to which heat inactivated fetal bovine serum was added for 10% v/v final concentration (all from MediaTech Inc., Hemdon, Va.). Serum free medium was identical to culture medium but without 10% fetal bovine serum. As CHO-K1 is an attachment cell line, routine passage and other instances of cell harvest required detachment of cells from culture vessels. This was accomplished with 0.25% trypsin/2.21 mM EDTA solution (from MediaTech Inc.).

The metabolic activation system consisted of 1 part rat liver S9 post-mitochondrial fraction (Molecular Toxicology, Boone, N.C.) and 2.3 parts cofactor mixture. The cofactor mixture was β-NADP at 20 mg/ml and DL-isocitric acid at 85 mg/ml dissolved in serum free medium (pH adjusted to approximately 7.2 with 1 N NaOH).

Heat Shock

Apoptosis was induced in log phase L5178Y cells by placing a flask in a dry 47° C. oven for 1 hr. During this 1 hr period, the flask was tightly sealed. After this heat shock treatment, the culture was returned to a 37° C. incubator with 5% $CO_2$, thereby allowing the apoptotic program to progress. At 1 hr intervals, cells were harvested and incubated with each of the following four reagents in order to evaluate the percentage of dead cells: YO-PRO-1 (Idziorek et al., "YOPRO-1 Permits Cytofluorometric Analysis of Programmed Cell Death (Apoptosis) Without Interfering With Cell Viability," *J. Immunological Methods* 185:249-258 (1995), which is hereby incorporated by reference in its entirety), Annexin-PE (Vermes et al., "A Novel Assay for Apoptosis. Flow Cytometric Detection of Phosphatidylserine Expression on Early Apoptotic Cells Using Fluorescein Labelled Annexin V," *J. Immunol. Meth.* 184:39-51 (1995), which is hereby incorporated by reference in its entirety), propidium iodide (Darzynkiewicz et al., "Cytometry in Cell Necrobiology: Analysis of Apoptosis and Accidental Cell Death (Necrosis)," *Cytometry* 27:1-20 (1997), which is hereby incorporated by reference in its entirety), and EMA (Riedy et al., "Use of a Photolabeling Technique to Identify Nonviable Cells in Fixed Homologous or Heterologous Cell Populations," *Cytometry* 12:133-139 (1991), which is hereby incorporated by reference in its entirety). Flow cytometry analysis (488 nm excitation) was performed and the percentage of fluorochrome-positive cells was calculated based on the acquisition of 20,000 total cells per sample.

This same heat shock procedure was used in a subsequent experiment to generate a culture with a high frequency of apoptotic cells (i.e., 1 hr heat treatment, 2 hrs of progression at 37° C.). The heat shocked culture was then added to healthy log phase cells at various ratios. These cultures were processed for flow cytometry scoring of micronuclei using the EMA-SYTOX labeling method described infra.

Chemical Treatment and Cytotoxicity Measurements

L5178Y cells were treated over a range of chemical concentrations in culture medium, one 25 $cm^2$ flask per concentration. During treatment, cells were at $3 \times 10^5$/ml in a volume of 20 ml per flask (this high number of cells facilitated multiple readings per flask). After a 4 hr treatment period, cells were washed one time via centrifugation at 600×g, resuspended in a volume of 40 ml culture medium, and transferred to 75 $cm^2$ flasks. Cells were re-incubated at 37° C. for 20 additional hrs—the equivalent of two normal doubling times. For treatments that involved the promutagens benzo[a]pyrene and cyclophosphamide, the 4 hr treatment period was conducted in the presence of 10% v/v metabolic activation system.

L5178Y cells were also exposed to the chemicals sucrose, tributyltin methoxide, dexamethasone, and vinblastine were also evaluated with a 24 hr exposure protocol. In this case, cultures ($1.5 \times 10^5$ cells/ml, 40 ml/flask) were continuously exposed to chemical over a range of concentrations. Cells were harvested after 24 hrs of incubation at 37° C. without recovery.

On the day before treatment, CHO-K1 cells were harvested and counted, and their density was adjusted to $6 \times 10^4$/ml in culture medium. This cell suspension was added to 75 $cm^2$ flasks (20 ml per flask; one flask per exposure group). After incubating for approximately 16 to 24 hrs at 37° C., spent culture medium was replaced with 20 ml fresh, pre-warmed medium per flask. Methyl methanesulfonate was added from 1000× strength stock solutions for final concentrations of 0, 10, 20, 30, and 40 µg/ml, at which time cultures where reincubated at 37° C. After a 4 hr treatment period, culture medium was aspirated, cells were rinsed one time with an isotonic salt solution, and then 20 ml fresh, pre-warmed culture medium was added to each flask. These cultures were reincubated for a 20 hr recovery period. At the time of cell harvest, 2.5 ml typsin/EDTA solution per flask was used to detach cells from culture vessels. Cells were collected via centrifugation and responded in culture medium.

Once L5178Y or CHO-K1 cells were collected as described above, cytotoxicity measurements were performed as follows: 0.5 ml of each culture was added to flow cytometry tubes containing fluorescein diacetate ("FDA") (0.075 µg/ml), propidium iodide ("PI") (25 µg/ml), and 2.5 µm Carmine 580/620 microspheres (Molecular Probes, Eugene, Oreg.). The concentration of these "counting beads" was determined with a hemacytometer. This facilitated calculation of the absolute number of live (FDA+) and dead (PI+) cells via flow cytometric analysis (Brando et al., "Cytofluorometric Methods for Assessing Absolute Numbers of Cell Subsets in Blood," *Cytometry* 42:327-346 (2000), which is hereby incorporated by reference in its entirety). Relative survival was then calculated as follows: The number of FDA+ cells in each chemical treatment culture was expressed as a percentage of the number of FDA+ cells in the concurrent solvent control culture. Only those treated flasks that exhibited ≦60% reduction to relative survival were prepared for microscopy- and flow cytometric-based micronucleus analyses as described infra. Sucrose was tested up to 5 mg/ml, as significant cytotoxicity was not observed.

Flow Cytometric Scoring of Micronuclei: Cell Harvest, Staining and Lysis

At the time of cell harvest, FDA+ and PI+ cell counts were performed as described supra. For each culture which exhibited ≦60% reduction to FDA+ cells relative to solvent control, $1.5 \times 10^6$ total cells were transferred to each of three 15 ml centrifuge tubes (to provide three independently stained and flow cytometric-analyzed specimens per flask). Cells were collected via centrifugation at approximately 600×g for 5 minutes. Supernatants were aspirated, and cells were resuspended with gentle tapping. 200 µl "Buffer Solution" (PBS with 2% heat-inactivated fetal bovine serum, both from MediaTech) was added to each tube and cells were then transferred to flow cytometry tubes (transparent polystyrene) with 100 µl Nuclei Acid Dye 1 Solution (0.125 mg/ml EMA prepared in Buffer Solution). These tubes were placed in racks and submerged to a depth of approximately 2 cm in crushed ice. A visible light source (60 watt light bulb) was positioned approximately 30 cm above the tubes for 20 minutes.

After the photoactivation period, 800 µl cold buffer solution was added to each sample. From this point forward, exposure of samples to light was minimized with dim lighting and foil. The contents of the tubes were then transferred to 15 ml polypropylene centrifuge tubes, and 8 ml of cold buffer solution was added to each sample. Cells were collected via centrifugation, and supernatants aspirated such that approximately 50 µl of supernatant remained per tube. Cells were gently resuspended with tapping, and were maintained at room temperature until the follow procedures were initiated (within 30 minutes). 1 ml "Lysis Solution 1" was added slowly to each tube (approximately 15 seconds per sample). Lysis Solution 1 was prepared with deionized water and 0.584 mg/ml NaCl, 1 mg/ml sodium citrate, 0.3 µl/ml IGEPAL, 1 mg/ml RNase A, and 0.2 µM SYTOX Green. Upon addition of Lysis Solution 1, the tube was immediately vortexed (medium setting) for 5 seconds. These samples were kept at room temperature for 1 hr. At this time, 1 ml "Lysis Solution 2" was injected forcefully into each tube, which were immediately vortexed (medium) for 5 seconds. Lysis Solution 2 was prepared with deionized water and 85.6 mg/ml sucrose, 15 mg/ml citric acid, and 0.2 µM SYTOX Green. These specimens were maintained at room temperature for 30 minutes. Subsequently, samples were stored at 4° C. until flow cytometric analysis (up to two days following cell harvest/staining/lysis procedures).

Flow Cytometric Scoring of Micronuclei: Instrumentation and Gating

Samples, stored for up to two days at 4° C., were gently tapped to resuspend the particles. Data acquisition and analysis was then accomplished with a single-laser flow cytometer, 488 nm excitation (FACSCalibur, BD Biosciences, San Jose, Calif.). Instrumentation settings and data acquisition/analysis were controlled with CellQuest software v3.3 (BD Biosciences). SYTOX-associated fluorescence emission was collected in the FL1 channel (530/30 band-pass filter), and EMA-associated fluorescence was collected in the FL3 channel (670 long-pass filter). Events were triggered on FL1 fluorescence. The FCM gating strategy that was developed for this micronuclei scoring application required events to meet each of six separate criteria before they were scored as nuclei or micronuclei (see FIGS. 2A-H). The incidence of flow cytometric-scored micronuclei is expressed as frequency percent (no. micronuclei/no. nuclei×100), and are based on the acquisition of 20,000 EMA-negative nuclei per specimen.

Microscopy-based Scoring of Micronuclei

Approximately $3.5 \times 10^6$ cells per culture were centrifuged and resuspended with 20 µl heat-inactivated fetal bovine serum. 5 µl aliquots were applied to glass slides. Air dried slides were submerged in absolute methanol for 10 minutes and then stored in the dark until staining and analysis. Staining was accomplished by submerging slides for 60 seconds in acridine orange solution (12.5 mg/ml, prepared in PBS). An Olympus BH-2 fluorescence microscope was used for micronuclei measurements at 400× magnification. For each treated culture, 2000 mononucleated, non-apoptotic, non-necrotic cells were analyzed for the presence of micronuclei (1000 cells×2 slides per culture). To be scored as a micronuclei-containing cell, the micronuclei event(s) had to be approximately round in shape, exhibit similar staining characteristics as the main nucleus, less than ⅓ the size of the main nucleus, and could not overlap with the main nucleus. The incidence of micronucleated cells is presented as mean frequency percent.

Statistical Analyses

Mean % micronuclei and standard error of the mean ("SEM") values were calculated in Excel (Office X for Mac®, Microsoft Corp., Seattle, Wash.). To assess the degree to which mean flow cytometric-based % micronuclei data corresponded to parallel microscopy-based measurements, non-parametric Spearman's coefficients (rs) were calculated for each chemical studied (JMP Software, v5 for Mac®, SAS Institute, Cary, N.C.).

Example 1

Heat Shock Treatment

Figure 3:
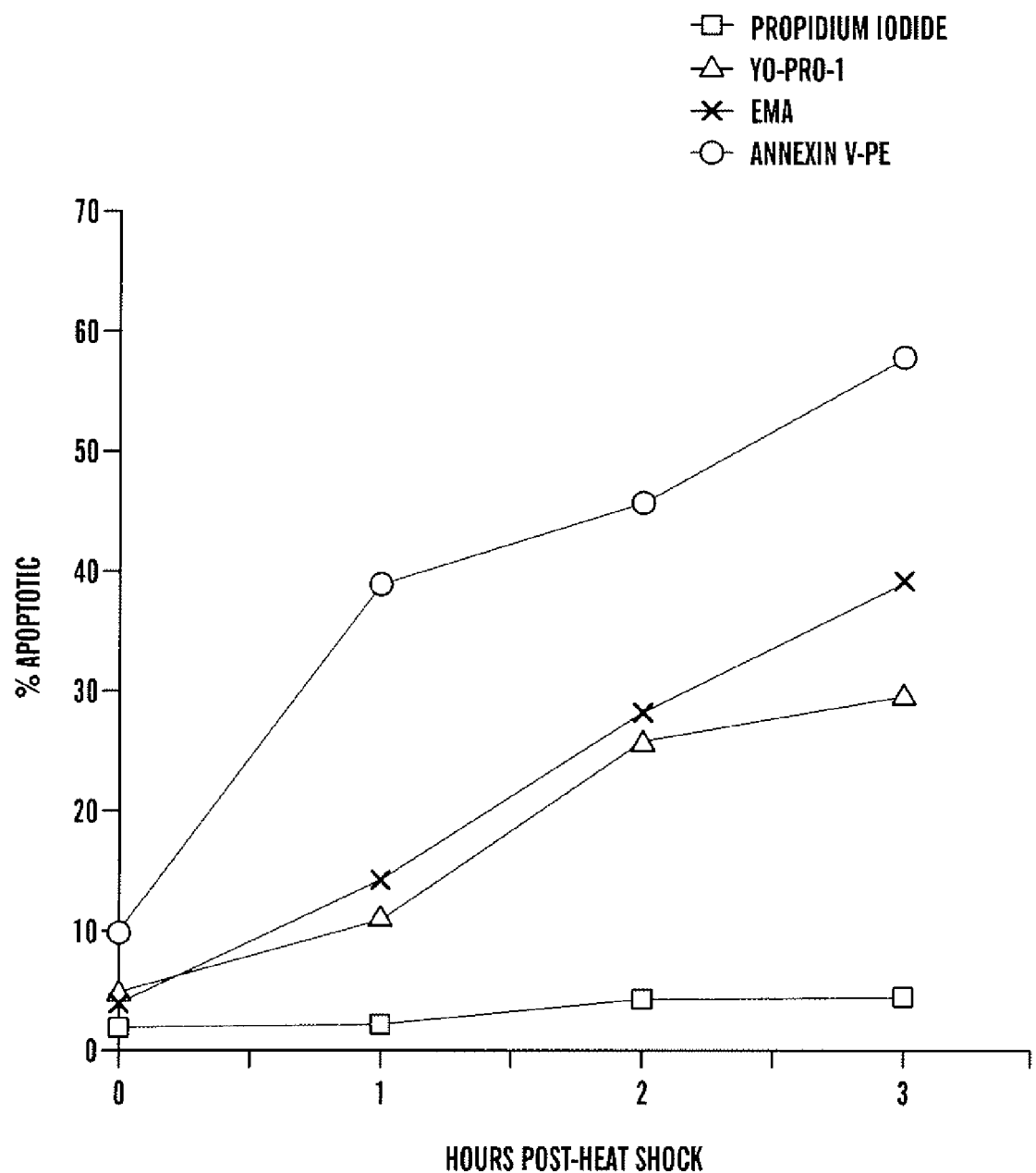
FIG. 3 is a graph showing apoptosis resulting from 1 hr heat treatment, as detected by four different staining techniques. These data illustrate the rates at which dying cells acquire these different staining characteristics. EMA is seen to be a relatively early indicator of apoptosis, as it rivals YO-PRO-1, a dye which is known to stain early stage apoptotic cells.

L5178Y cells were exposed to an elevated temperature ("heat shock") to evaluate the stage of apoptosis at which EMA staining occurs. Other more commonly used labeling techniques were studied to provide a frame of reference. Representative time-course data are presented in FIG. 3. As expected, cell surface expression of phosphatidyl serine, as demonstrated by Annexin V-labeling, occurred most rapidly in response to heat treatment. In contrast, exclusion of the charged nucleic acid dye propidium iodide was only modestly affected over this time-course. Relative to annexin and propidium iodide, an intermediate rate of EMA-positive labeling was observed. In fact, EMA performed quite similarly to YO-PRO-1, a nucleic acid dye that has been described as a relatively early-stage apoptosis marker (Idziorek et al., "YOPRO-1 Permits Cytofluorometric Analysis of Programmed Cell Death (Apoptosis) Without Interfering with Cell Viability," *J. Immunol. Methods* 185:249-258 (1995), which is hereby incorporated by reference in its entirety).

Figure 4:
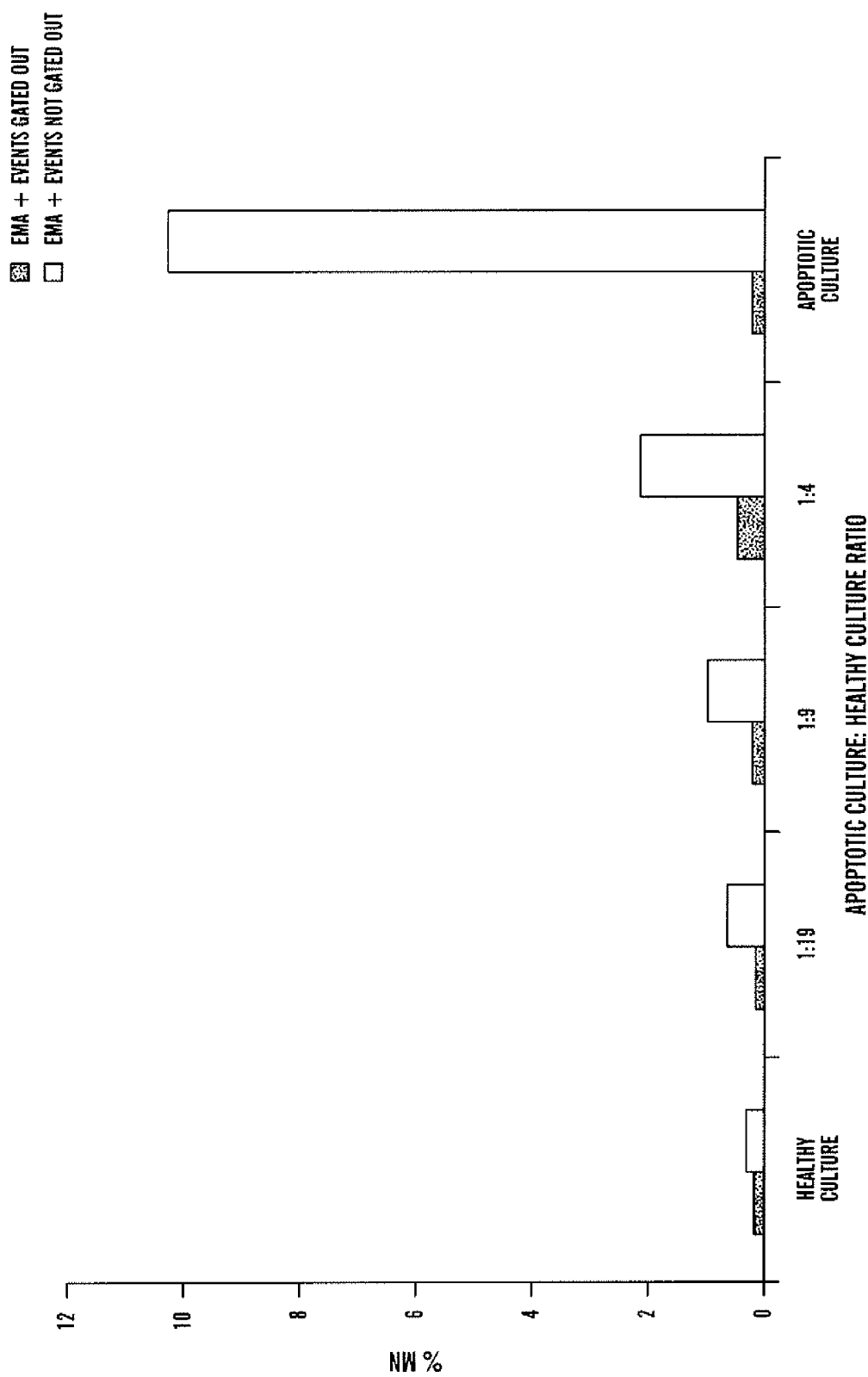
FIG. 4 is a graph showing micronuclei frequencies plotted against culture conditions. The "Healthy Culture" consisted of log phase L5178Y cells, whereas the "Apoptotic Culture" consisted of cells which were heat-treated. These cultures were combined, then processed for flow cytometric scoring. When the EMA staining criterion was not employed (white bars), the frequency of micronuclei was artificially high due to contamination of dead and dying cells' chromatin. On the other hand, the frequency of micronuclei was not appreciably affected when an EMA staining criterion was used to exclude chromatin from dead and dying cells (black bars).

A subsequent heat shock experiment evaluated the degree to which EMA staining, followed by detergent and SYTOX incubation, is able to differentially label micronuclei and apoptotic bodies. Micronuclei were scored via flow cytometry, with one exception to the standard procedure described above. For this experiment, micronuclei frequencies were determined for these preparations both with and without the EMA-staining gate/criterion (see FIG. 2F). As shown by FIG. 4, when flow cytometric analyses did not exclude EMA-positive events, chromatin from dead/dying cells was observed to significantly impact the micronuclei scoring region. Conversely, when EMA-positive particles were excluded from these analyses, baseline micronuclei frequencies were observed. These data support the hypothesis that EMA may be useful for protecting flow cytometric-based micronuclei counts from spuriously high readings due to the presence of dead and dying cells.

Example 2

Genotoxicants

Each of the six genotoxicants studied was observed to cause a dose-related increase in micronucleus frequency (FIGS. 5A-G). As demonstrated by the low degree of variation among replicate flow cytometric samples, reproducible % micronuclei values were observed for the automated scoring process for both vehicle and genotoxicant-treated cultures. Furthermore, the correspondence between flow cytometric- and microscopy-based values was high ($r_s$ values ranged from 0.7 to 1.0; see Table 2).

TABLE 2

Overview of Micronucleus Test Results (L5178Y Cells)

| Chemical | Treatment/Recovery (hrs) | Highest Conc. Tested (μg/ml) | MN Induction (≧3-fold) | FCM/Microscopy Spearman Correlation | Cell Cycle Effect* |
|---|---|---|---|---|---|
| Methyl methanesulfonate | 4/20 | 30 | Yes | 1.000 | +++ |
| Hydroxyurea | 4/20 | 18 | Yes | 0.9429 | +++ |
| Etoposide | 4/20 | 0.1 | Yes | 1.000 | ++ |
| Cyclophosphamide monohydrate | 4/20 | 6 | Yes | 1.000 | + |
| Benzo[a]pyrene | 4/20 | 4 | Yes | 0.9370 | − |
| Vinblastine sulfate | 4/20 | 0.3 | Yes | 0.7000 | +++ |
| Vinblastine sulfate | 24/0 | 0.00075 | Yes | 1.000 | +++ |
| Tributyltin methoxide | 4/20 | 0.15 | No | 0.9487 | − |
| Tributyltin methoxide | 24/0 | 0.06 | No | 0.4104 | − |
| Dexamethasone | 4/20 | 300 | No | 0.2868 | − |
| Dexamethasone | 24/0 | 100 | No | −0.4472 | − |
| Sucrose | 4/20 | 5000 | No | 0.2236 | − |
| Sucrose | 24/0 | 5000 | No | 0.3482 | − |

*Qualitative assessment of SYTOX fluorescence histogram (− no difference relative to solvent control; +++ distinctly different).

The benzo[a]pyrene graph (FIG. 5E) shows flow cytometric-based solvent control % micronuclei values that are moderately elevated relative to parallel microscopy and other flow cytometric-based solvent control data sets. This experiment was performed early in the assay development process, and these elevated counts are attributable to unoptimized cell processing. Specifically, just prior to flow cytometry analysis, nuclei/micronuclei particles were resuspended with a pipettor as opposed to gentle tapping. One likely explanation for these modestly elevated baseline counts involves the fate of metaphase chromosomes. The two-step lysis procedure provides mitotic chromosomes which form rather tightly associated bundles (confirmed by microscopic inspection). In this aggregate form, they do not impact the micronuclei scoring region. However, it has been found that at this point in the process, it is possible to disassociate metaphase chromosomes when specimens are handled too vigorously. When this occurs, liberated metaphase chromosomes, with their micronucleus-like DNA content, can affect micronuclei frequency measurements. This explanation is supported by experiments with colcemid (0-4 hr treatments to accumulate cells in metaphase). Flow cytometric analysis of these specimens produced baseline-like micronuclei frequencies, but only when particles are resuspended by gentle tapping as opposed to pipetting or vigorous vortexing.

Figure 5A:
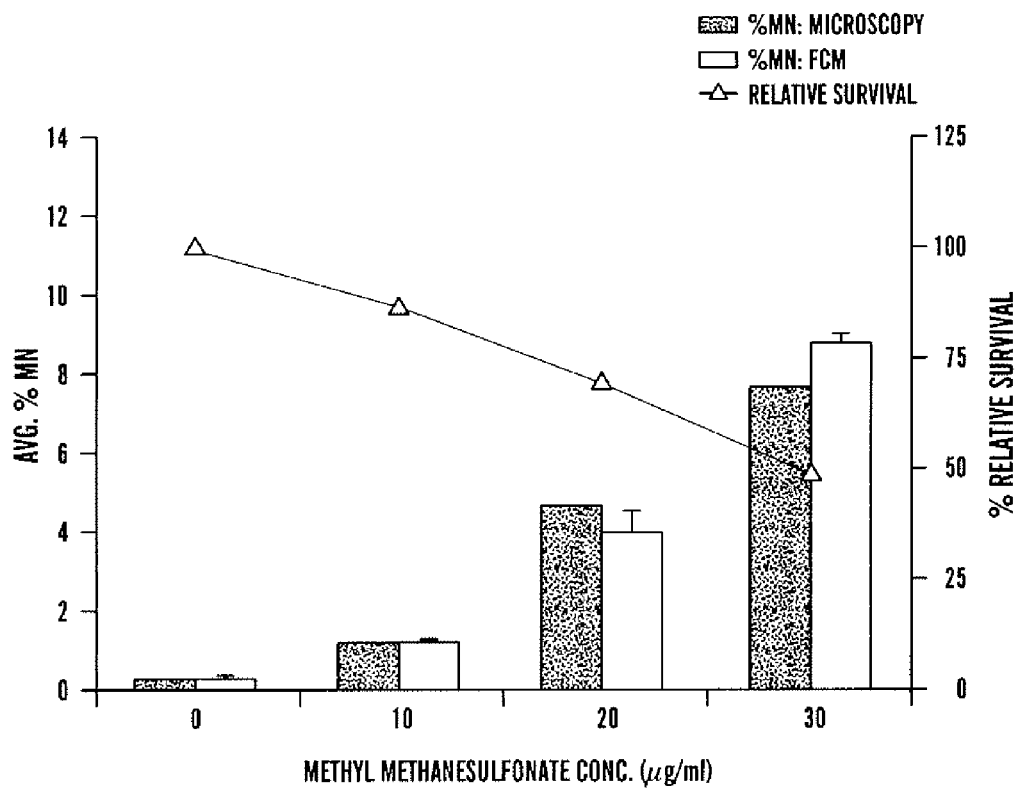
FIGS. 5A-M are graphs showing genotoxicity and cytotoxicity measurements for L5178Y cells treated with each of 9 chemicals. The Y-axis depicts the mean frequency of micronuclei obtained by microscopic inspection (black bars, 2000 cells scored per culture) and via flow cytometric (FCM) analysis (white bars, mean of 3 measurements per culture, with SEM bars). An index of cytotoxicity (% relative survival) is displayed on the YY-axis. Cells were treated for 4 hrs and harvested for analysis after an additional 20 hr recovery for experiments depicted by FIGS. 5A, 5B, 5C, 5D, 5E, 5F, 5H, 5J, and 5L. Treatment was continuous (24 hrs, no recovery) for experiments depicted in FIGS. 5G, 5I, 5K, and 5M.
Figure 5B:
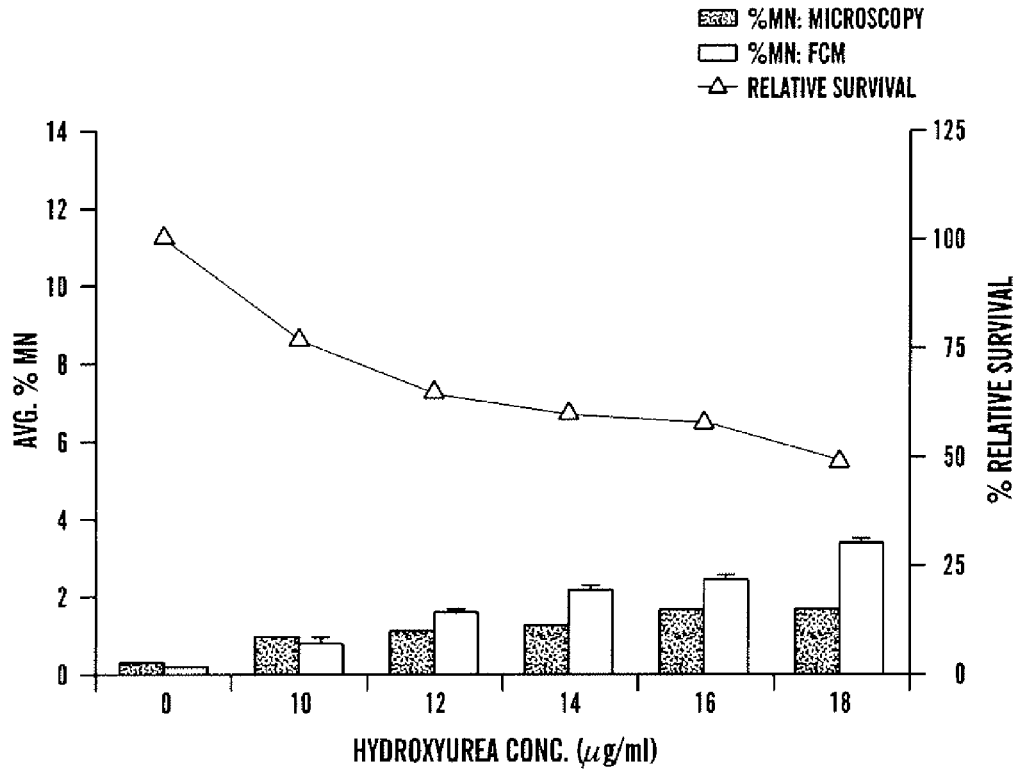
Figure 5C:
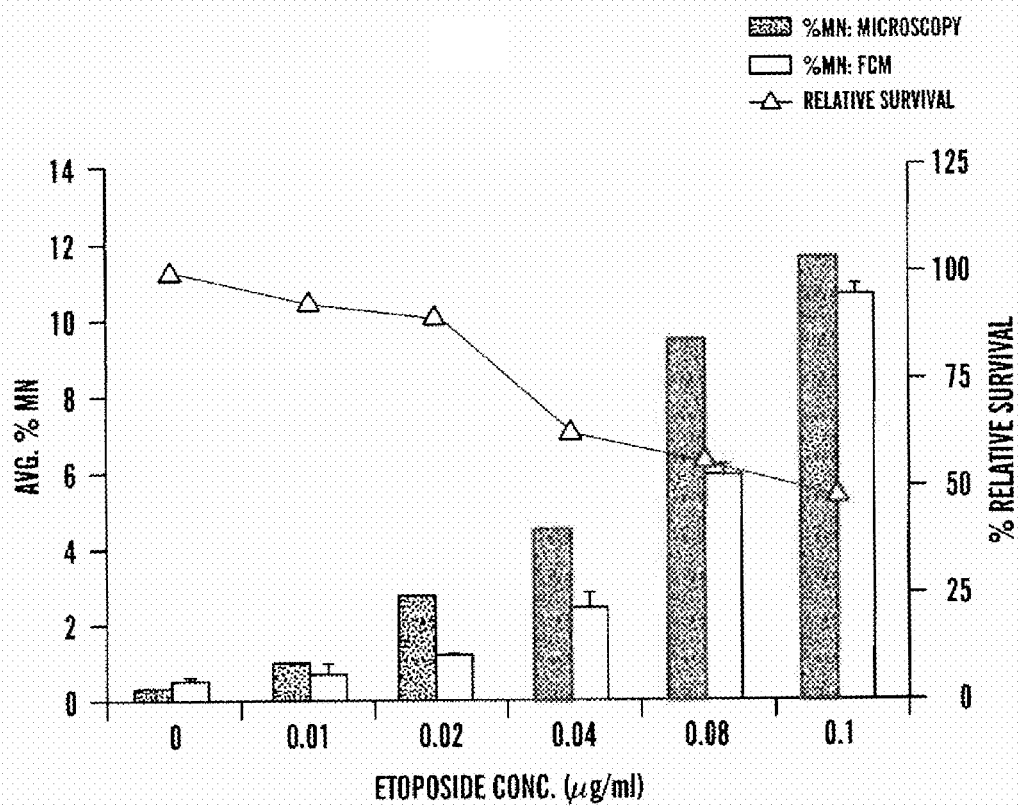
Figure 5D:
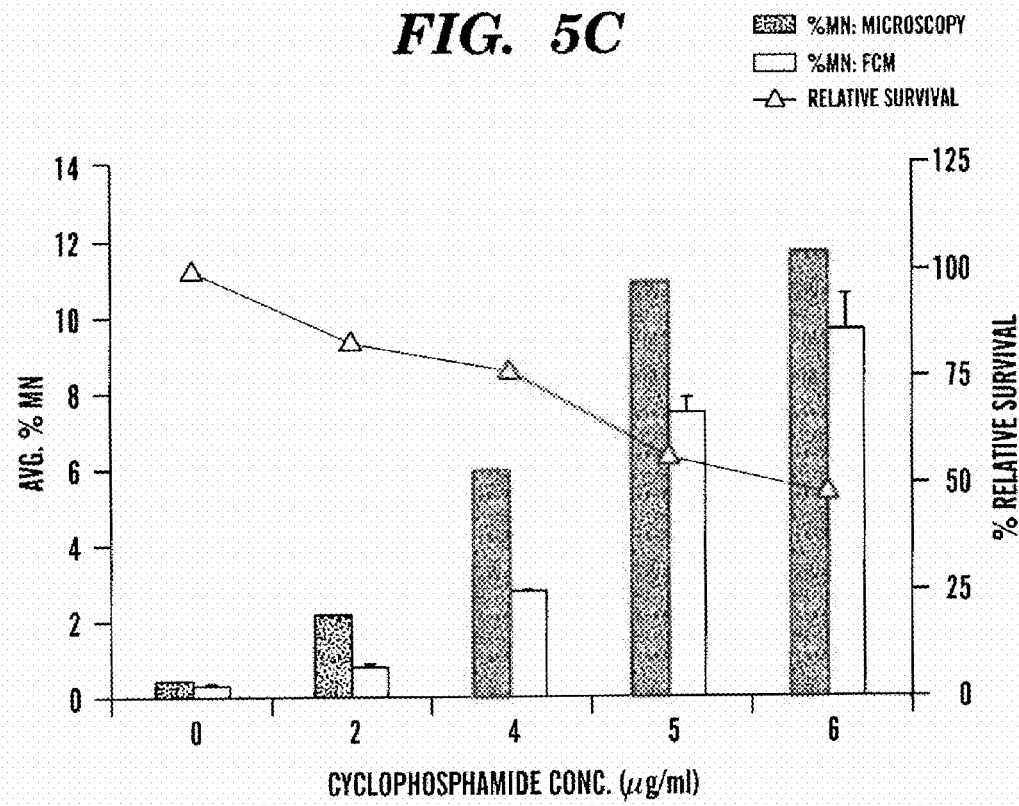
Figure 5E:
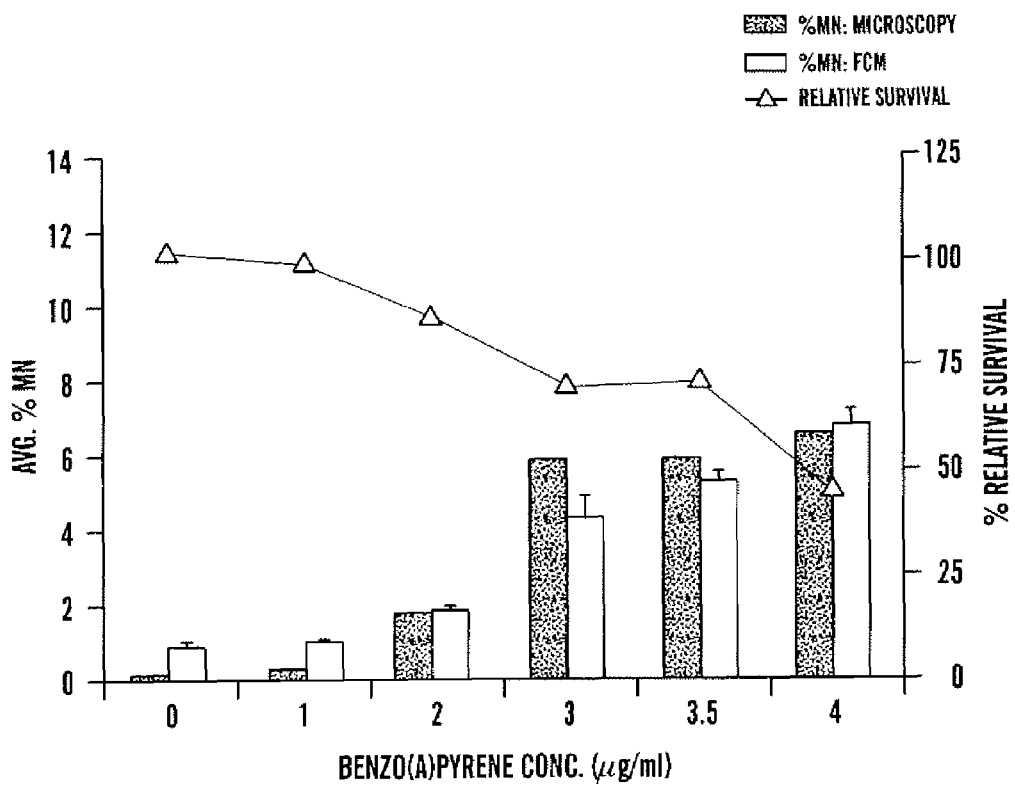
Figure 5F:
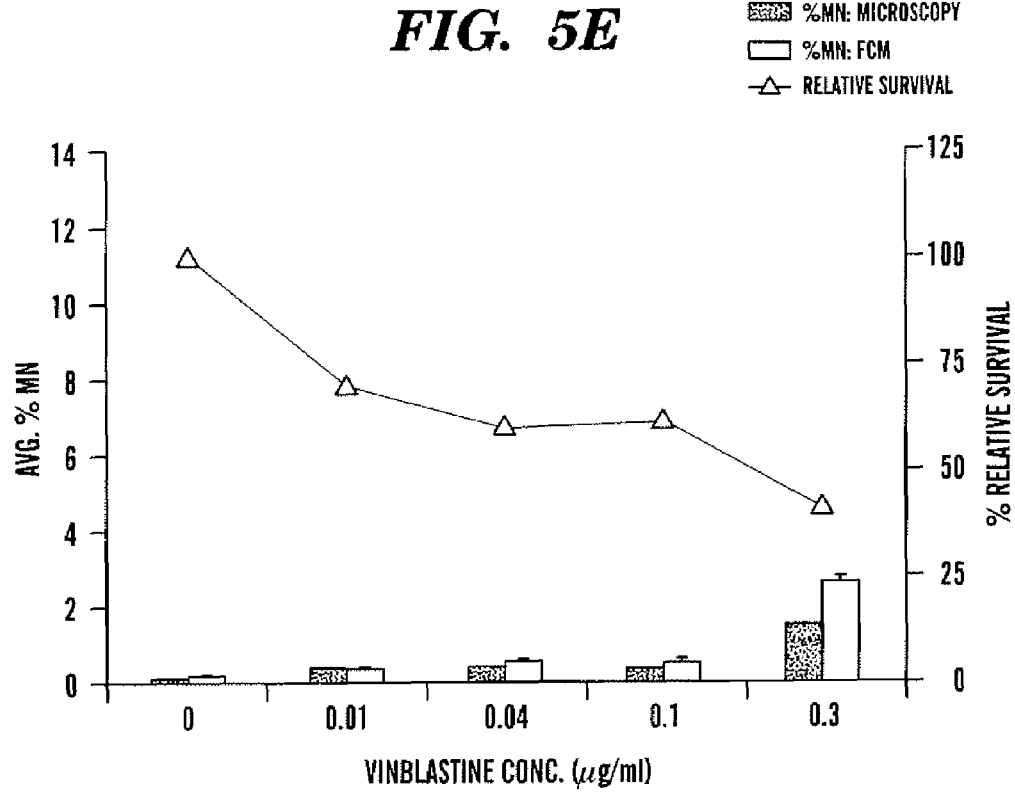
Figure 5G:
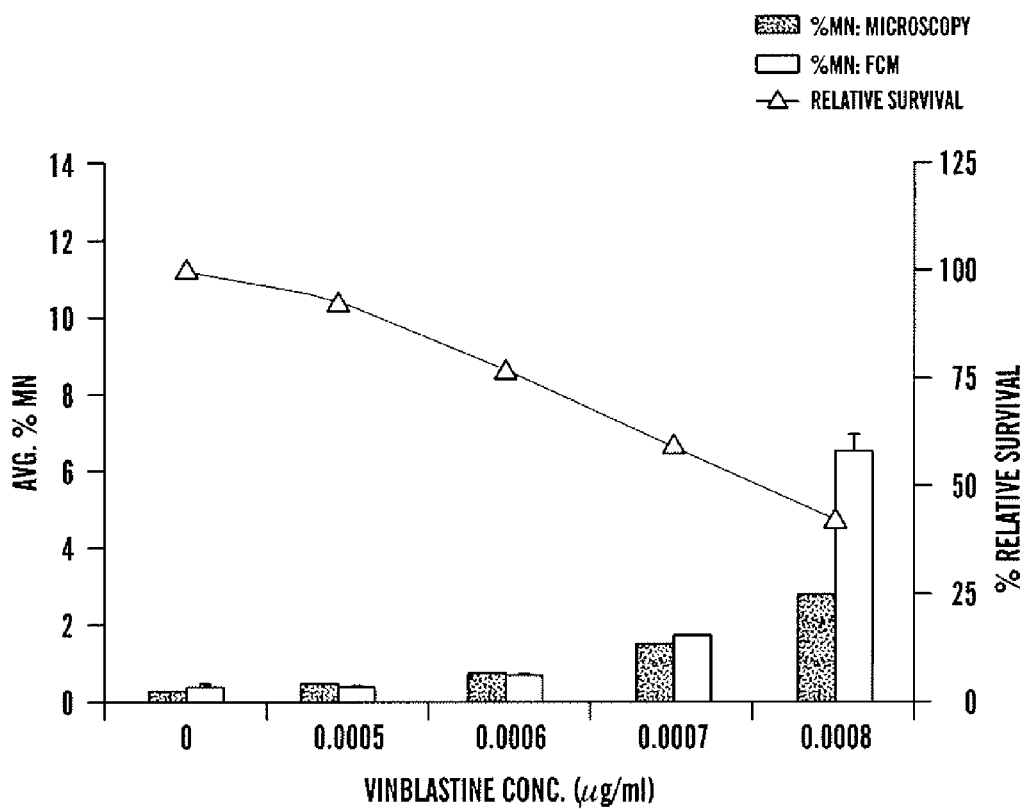

Given reports that some non-DNA reactive genotoxicants may require extended treatment durations to maximally express micronuclei (Matsushima et al., "Validation Study of the In Vitro Micronucleus Test in a Chinese Hamster Lung Cell Line (CHL/IU)," *Mutagenesis* 14:569-580 (1999), which is hereby incorporated by reference in its entirety) vinblastine was studied with a 24 hr continuous exposure in addition to the short-term treatment schedule. As shown by FIGS. 5F-G, the vinblastine-induced micronucleus response was indeed greater given the continuous exposure scheme. The discrepancy in micronucleus response observed at the highest concentration of this potent aneugen may be related to the difficulty of scoring slides noted by the microscopist at this cytotoxic drug level.

Example 3

Non-Genotoxicants

Figure 5H:
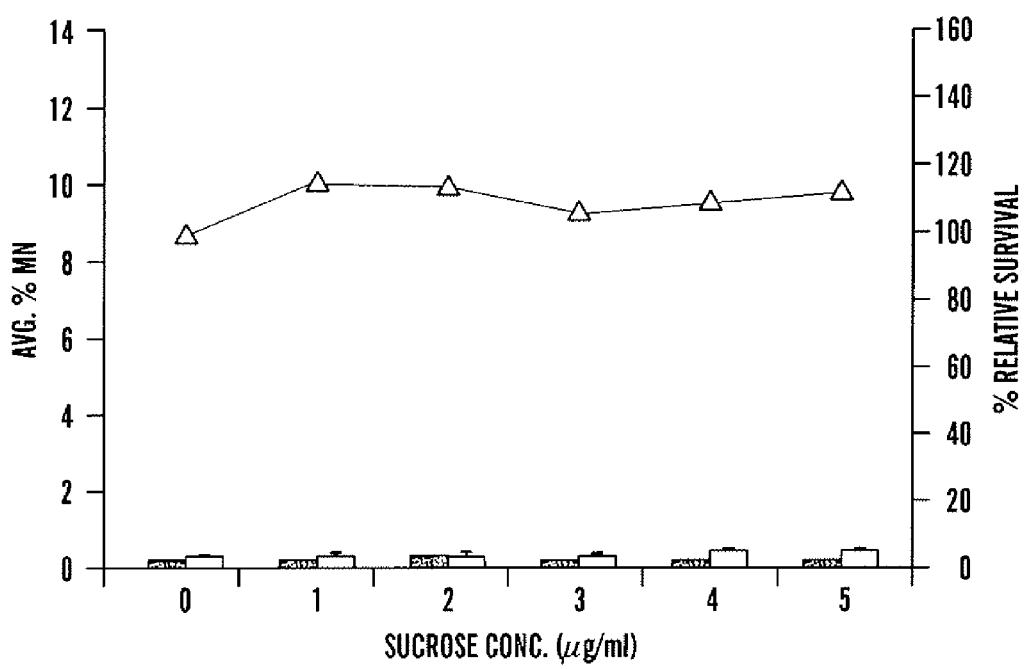
Figure 5I:
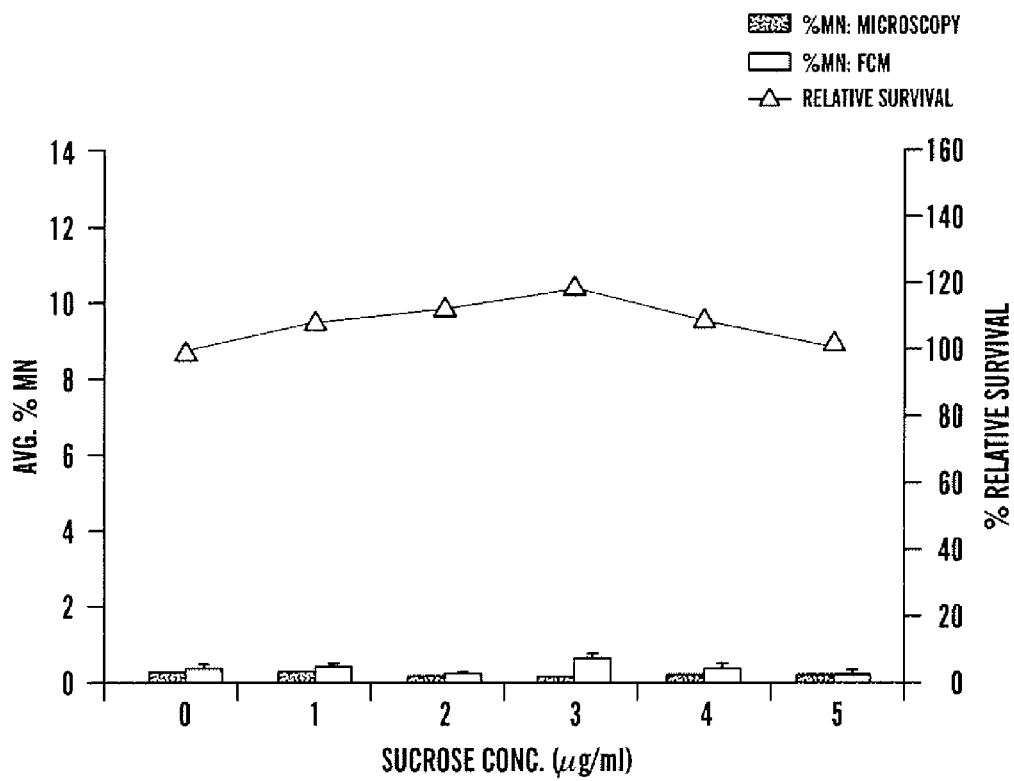
Figure 5J:
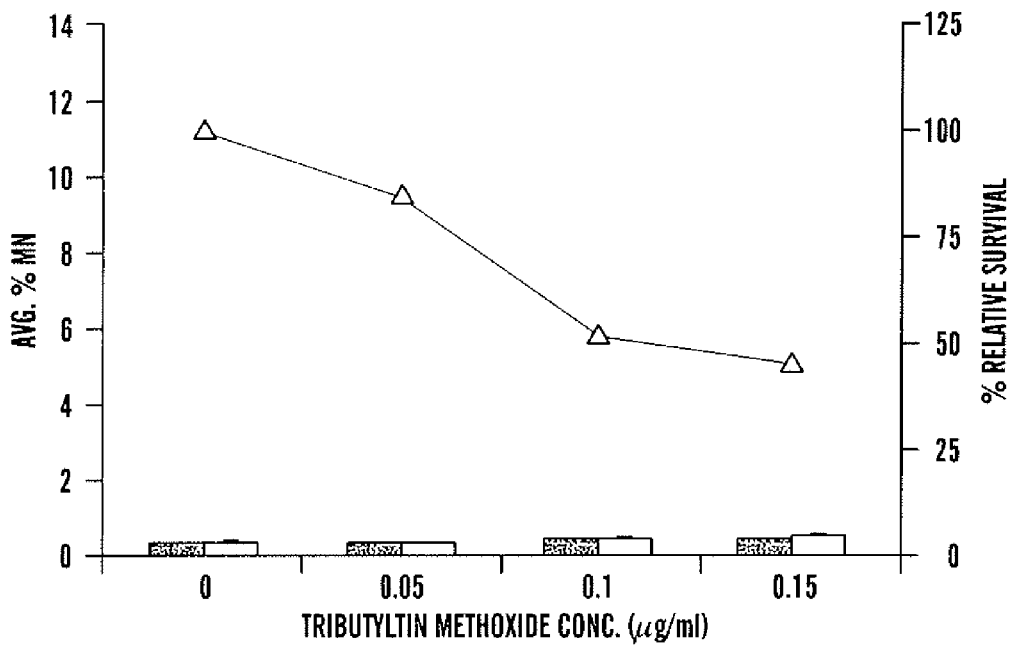
Figure 5K:
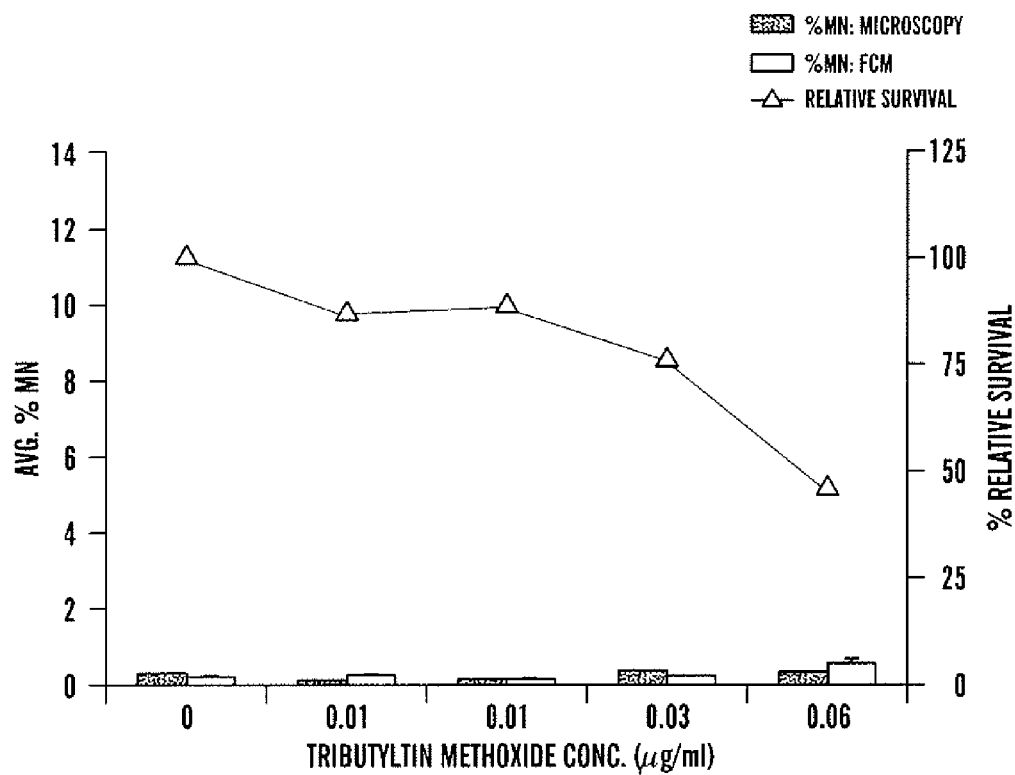
Figure 5L:
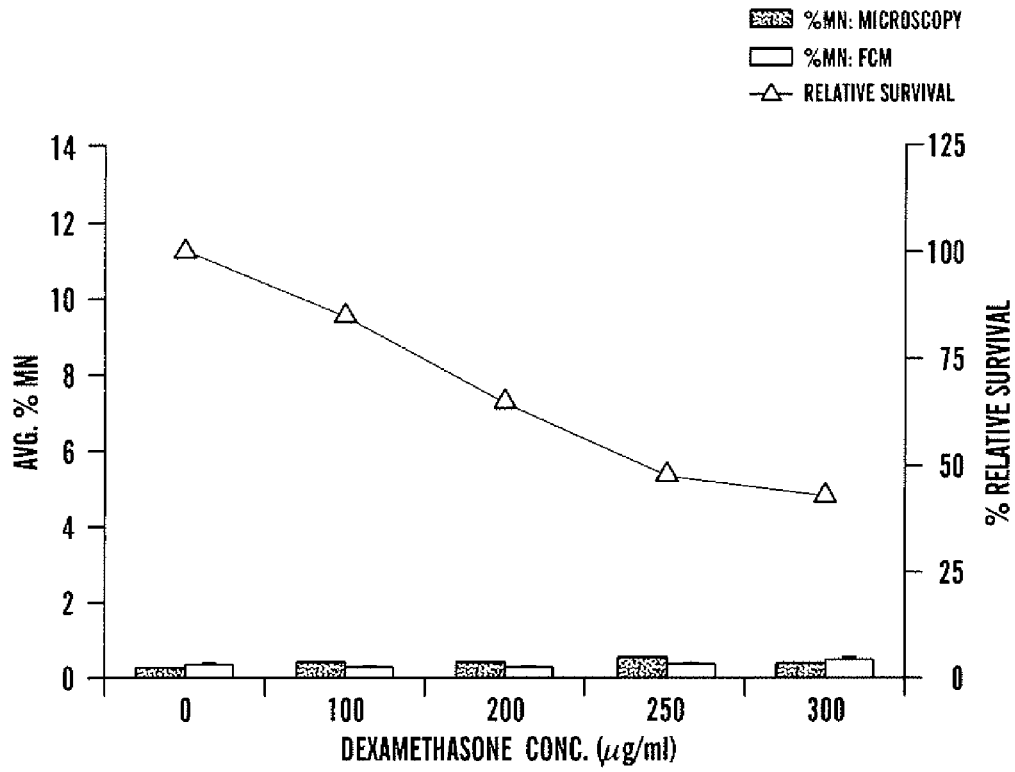
Figure 5M:
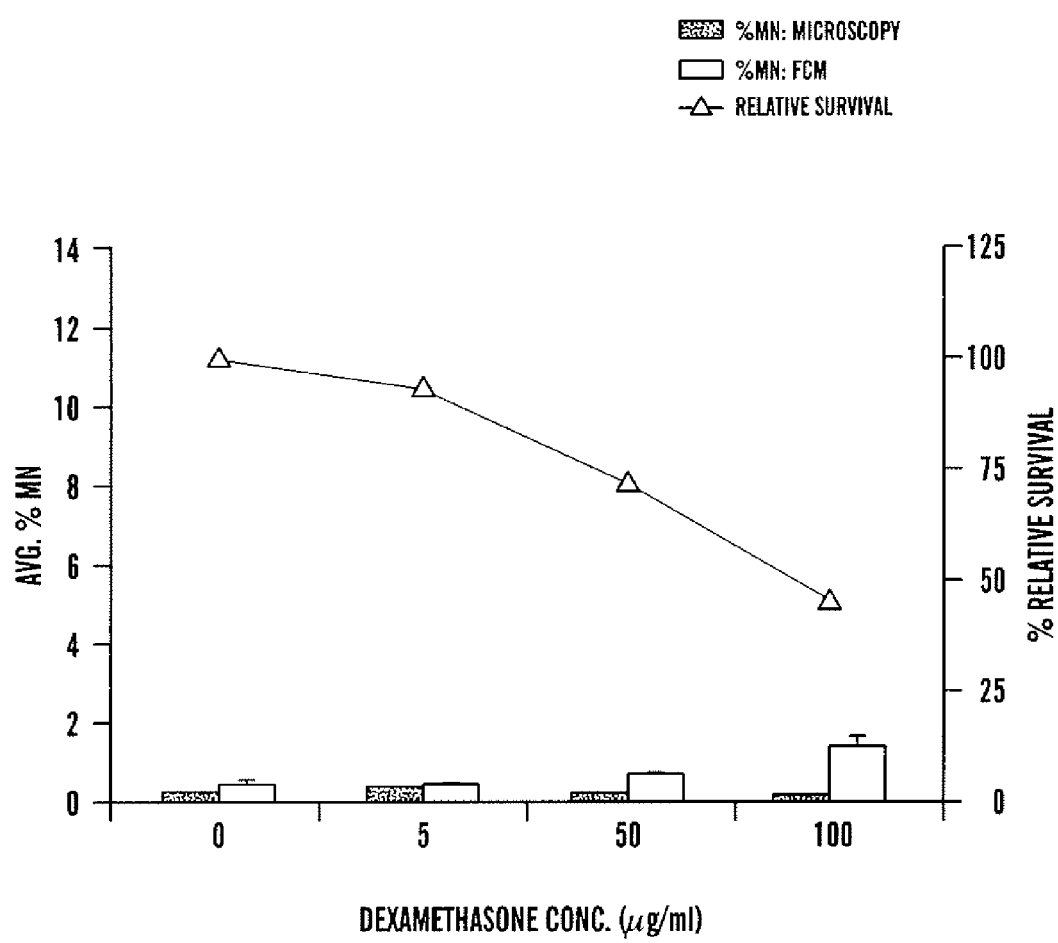

As shown in FIG. 5H, sucrose was neither cytotoxic nor genotoxic up to 5 mg/ml in the short-term exposure scenario. Based on expert working group recommendations, negative short-term results were followed by a continuous-treatment exposure (Kirsch-Volders et al., "Report from the In Vitro Micronucleus Assay Working Group," *Mutat. Res.* 540:153-163 (2003), which is hereby incorporated by reference in its entirety). Again, micronucleus-induction was not evident (see FIG. 5I). Correlation to microscopy is poorly depicted by the $r_s$ values that appear in Table 2. This may be explained by the extreme sensitivity of this statistic when % micronuclei frequencies are fluctuating in the range of baseline values.

The apoptosis-inducing agents tributyltin methoxide and dexamethasone were also investigated in both short-term and continuous exposure scenarios. Unlike sucrose, these experiments included concentrations which significantly affected cell survival (FIGS. 5J-M). Nil to slight changes in % micronuclei were observed for these chemicals even at cytotoxic concentrations. Both exposure scenarios resulted in less than 3-fold increase relative to solvent control. Continuous exposure resulted in fold increases which more closely approached this a priori cutoff. If this becomes a common finding as more non-genotoxicants are studied, it may be advantageous to explore the sensitivity and specificity of the assay when the cytotoxicity-based limit concentration for long-term treatments is lower than for short-term treatments. Another option may be to use additional criteria for setting the top concentration (for example % EMA-positive events, discussed in more detail, infra).

In any event, the tributyltin methoxide and dexamethasone data presented herein suggest that the EMA/SYTOX sequential staining method provides an effective layer of protection from spurious events derived from dead and dying cells. The system's relative insensitivity to appreciable levels of cytotoxicity is in stark contrast to tributyltin methoxide results reported by Nüsse et al., "Flow Cytometric Analysis of Micronuclei in Cell Cultures and Human Lymphocytes: Advantages and Disadvantages," *Mutat. Res.* 392:109-115 (1997), which is hereby incorporated by reference in its entirety, who used this chemical to demonstrate the unreliable nature of FCM-based micronuclei data in the context of apoptotic cultures.

Example 4

Supplemental Information: Cell Cycle

Figure 6A:
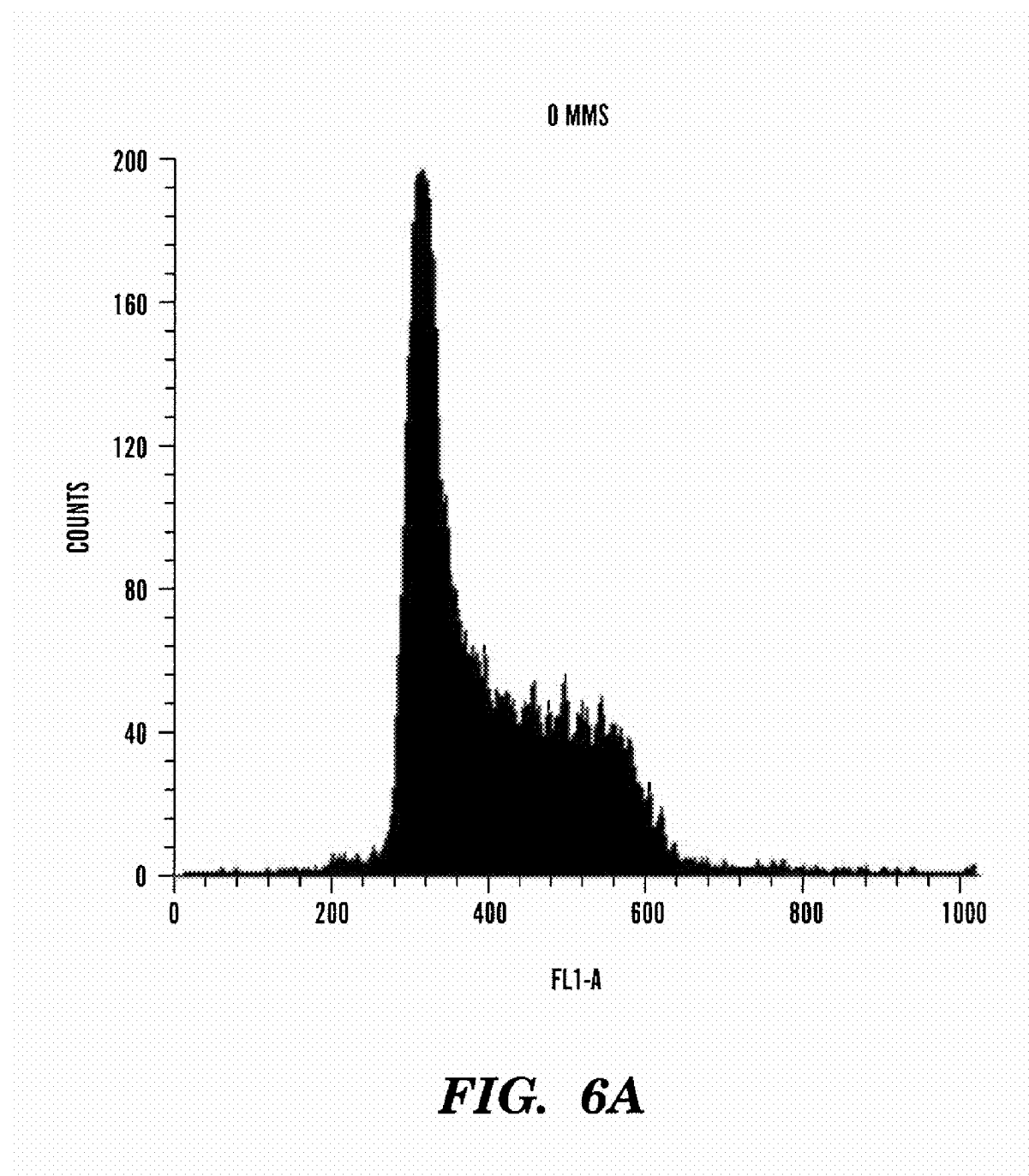
FIGS. 6A-C are graphs showing SYTOX-associated fluorescence (FL1-A) plotted for L5178Y cells treated with 0 (FIG. 6A), 10 (FIG. 6B), and 20 (FIG. 6C) µg methyl methanesulfonate (MMS) per ml. These data provide cell cycle information that is acquired simultaneously with micronucleus data. This example depicts a dose-dependent G2/M block.
Figure 6B:
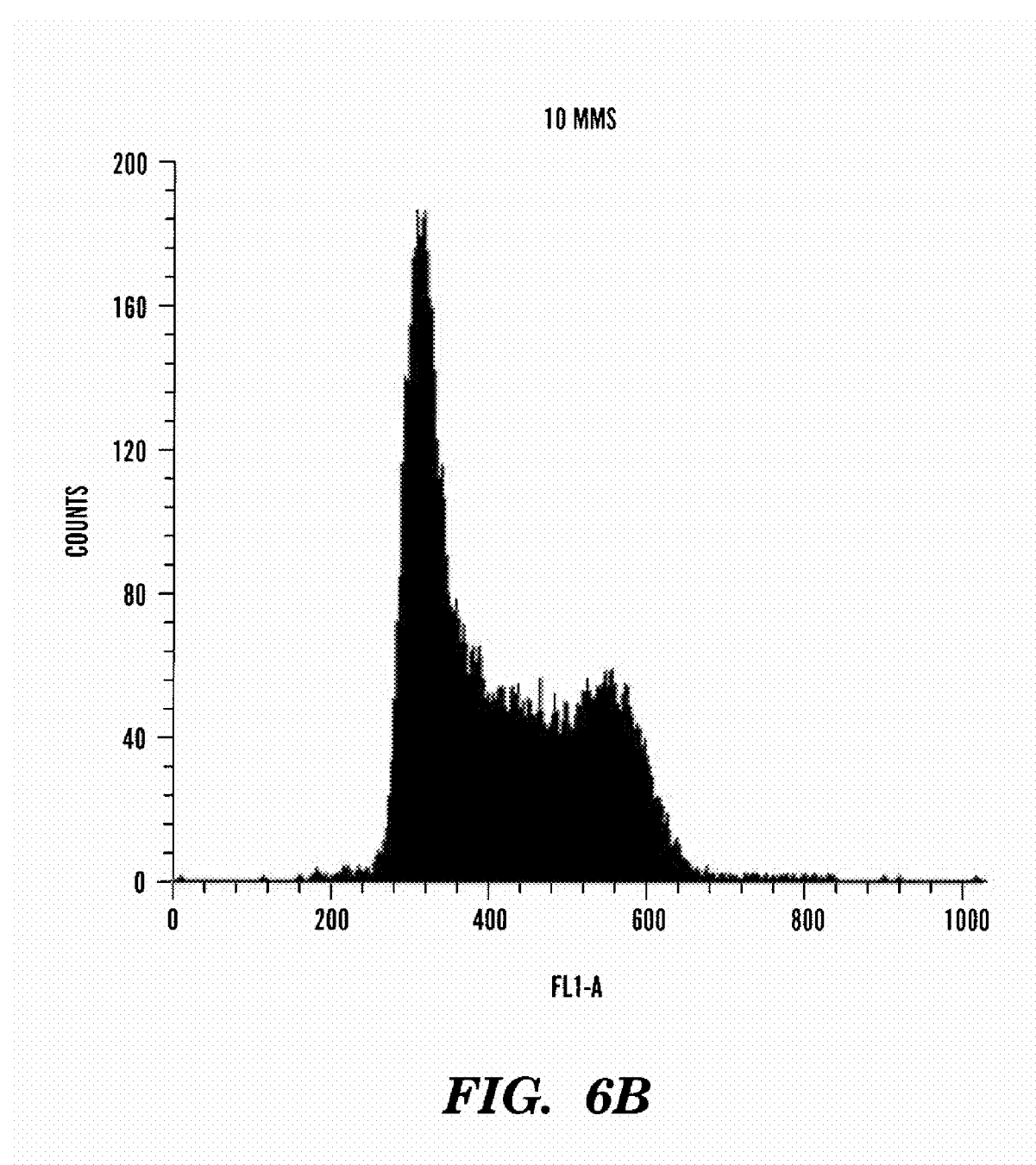
Figure 6C:
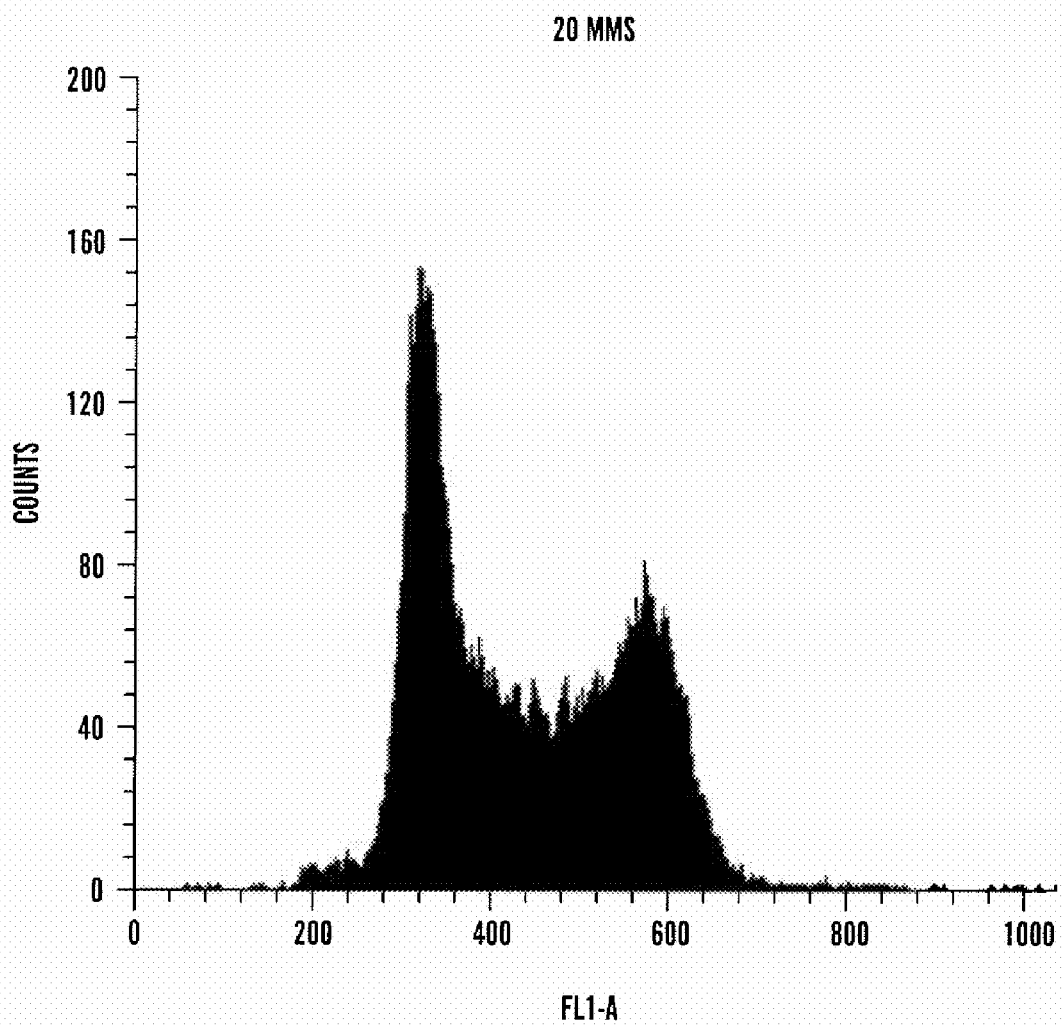
Figures 7A, 7B:
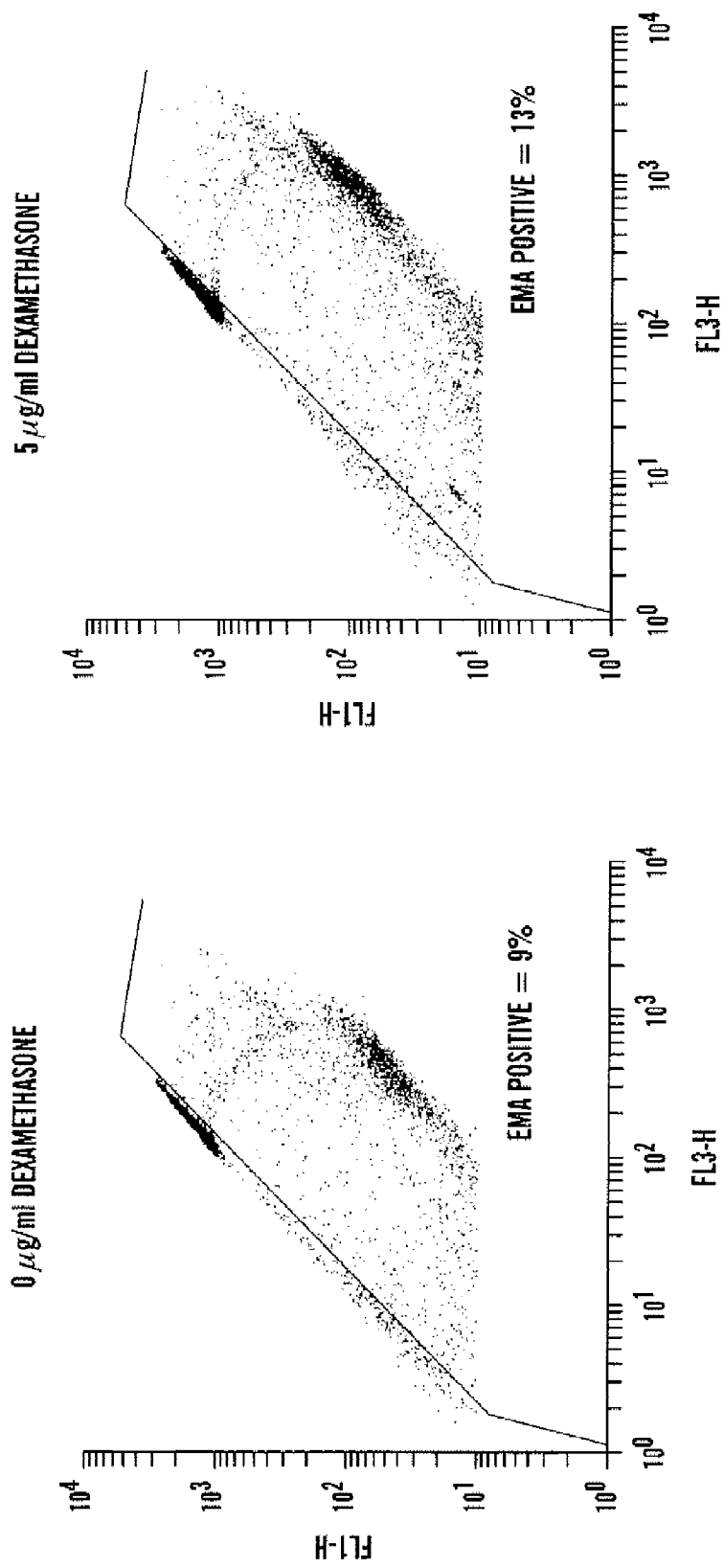
FIGS. 7A-D are graphs showing EMA versus SYTOX-associated fluorescence plotted for each of 4 dexamethasone-treated cultures (given 24 hr continuous treatment). The percent EMA-positive events is related to cell membrane integrity, and therefore provides supplemental cytotoxicity information that is acquired concurrently with flow cytometric micronucleus measurements.
Figures 7C, 7D:
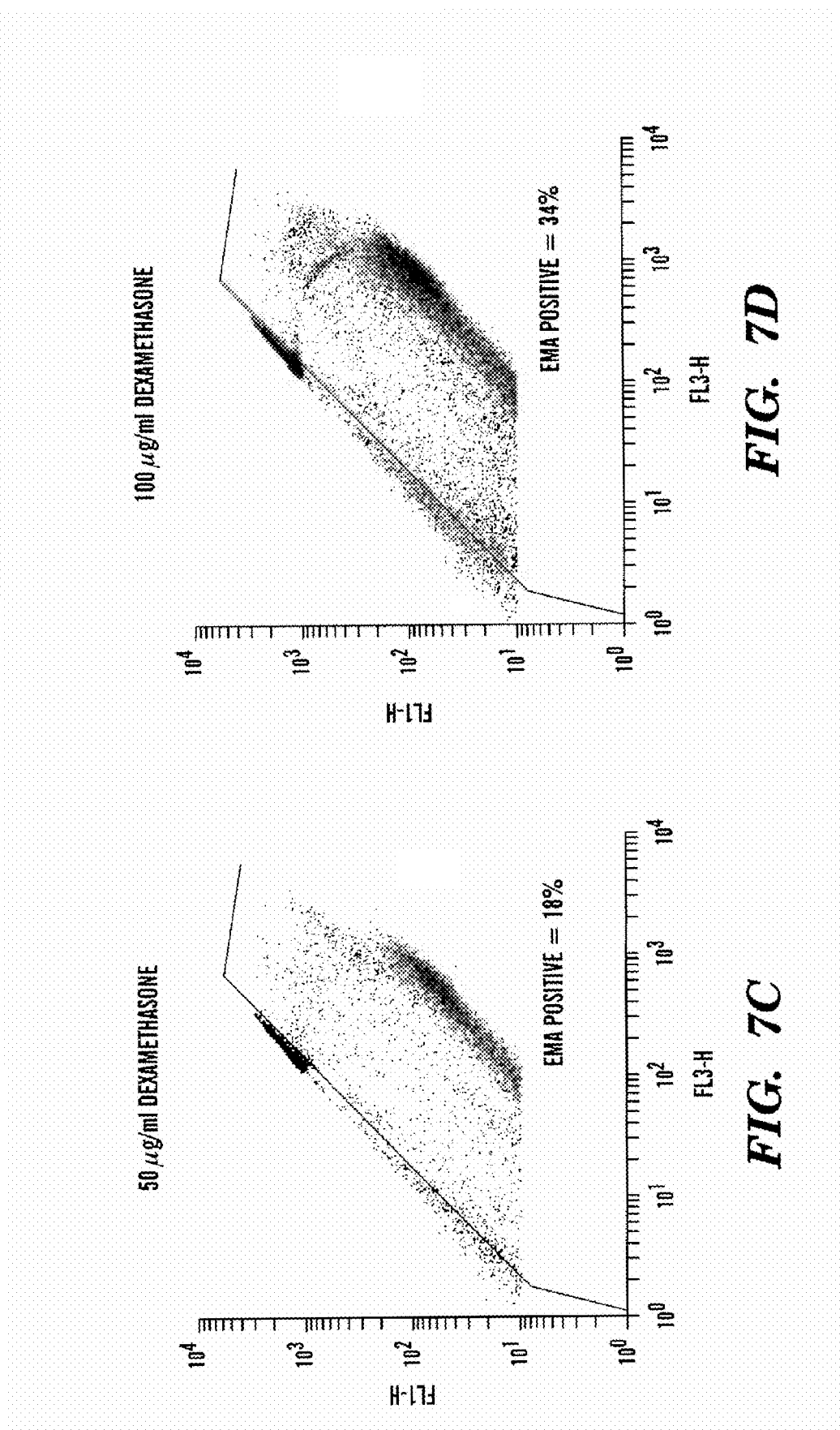

In addition to supplying micronuclei frequency data, it was found that flow cytometry could also provide concurrent information regarding cell cycle effects. That is, by displaying the SYTOX-associated signal as fluorescence area (FL1-A), qualitative assessments of cell cycle-related effects were possible. These analyses clearly demonstrated dose-dependent perturbations to cell cycle for each of the genotoxicants studied (see Table 2). For example, FIGS. 6A-C illustrate the G2/M block observed for short-term methyl methanesulfonate treatment. Note that while these observations are presented in a qualitative manner, software packages are available which are capable of deconvoluting such histograms to provide quantitative assessment of cell cycle effects.

Example 5

Supplemental Information: EMA-Positive Phenotype

In addition to supplying genotoxicity and cell cycle information, these flow cytometric analyses were capable of concurrently providing a measure of cytotoxicity. Specifically, the frequency of EMA-positive events is a statistic that relates to membrane integrity. For instance, except for non-cytotoxic sucrose, each of the other chemicals studied was observed to cause a dose-dependent increase in % EMA-positive events (see FIGS. 7A-D). This statistic could be useful for helping to identify chemical concentrations that are too cytotoxic for reliable genotoxicity assessment.

Example 6

Second Cell Line

Figure 8:
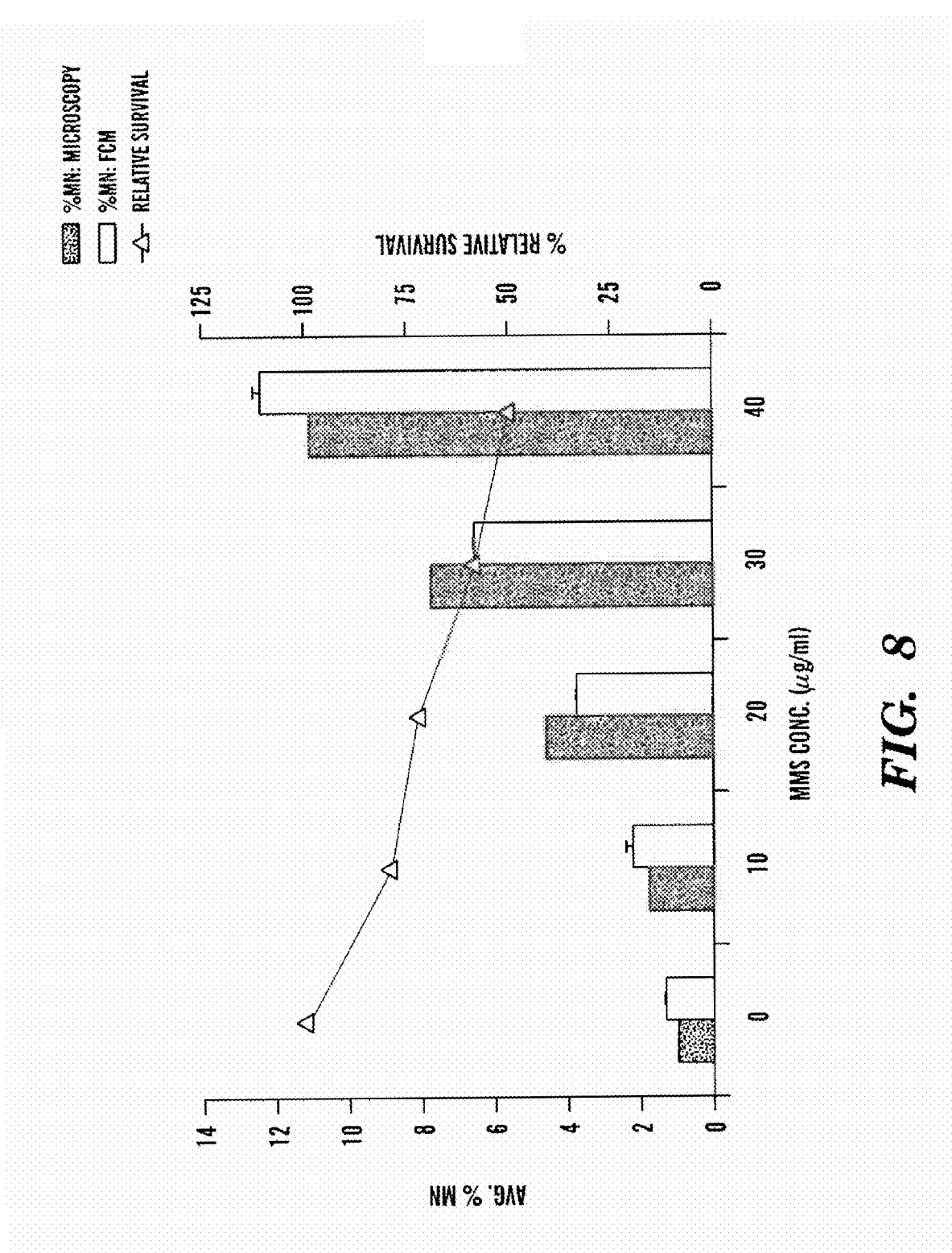
FIG. 8 is a graph showing genotoxicity and cytotoxicity measurements for CHO-K1 cells treated with a range of methyl methanesulfonate concentrations. The Y-axis depicts the mean frequency of micronuclei obtained by microscopic inspection (black bars, 2000 cells scored per culture) and via flow cytometric (FCM) analysis (white bars, mean of 3 measurements per culture, with SEM bars). An index of cytotoxicity (% relative survival) is displayed on the YY-axis. Cells were treated for 4 hrs and harvested for analysis after an additional 20 hr recovery.

CHO-K1 cells treated with methyl methanesulfonate exhibited a dose-related increase in micronucleus frequency (FIG. 8). As demonstrated by the low degree of variation among replicate flow cytometric samples, reproducible % micronuclei values were observed for the automated scoring process for both vehicle and genotoxicant-treated cultures. Furthermore, the correspondence between flow cytometric- and microscopy-based values was high ($r_s$ value=1.0). The morphology and growth characteristics of CHO cells are quite different from L5178Y (the former is an attachment cell line with fibroblast-like appearance, while the latter grows as a suspension culture with a lymphoblastoid-like appearance). Nonetheless, these mammalian cells that exhibit different morphologies and that originated from different species were found to be compatible with the cell staining, lysis, and flow cytometric analysis procedures described herein. Collectively, these data provide strong evidence of a robust scoring system.

CONCLUSIONS

Past concerns regarding the degree to which apoptosis adversely affects flow cytometry-based measurements were clearly warranted (Viaggi et al., "Flow Cytometric Analysis of Micronuclei in the CD2+ Subpopulation of Human Lymphocytes Enriched by Magnetic Separation," *Int. J. Radiat. Biol.* 67:193-202 (1995); Nüsse et al., "Flow Cytometric Analysis of Micronuclei in Cell Cultures and Human Lymphocytes Advantages and Disadvantages," *Mutat. Res.* 392: 109-115 (1997), which are hereby incorporated by reference in their entirety). The present data reinforces this contention, and also provides a procedure for minimizing or substantially eliminating this problem. The EMA/SYTOX procedure provided reproducible flow cytometry-based micronuclei measurements that correspond well to parallel microscopy-based values, even when chemicals were tested to cytotoxic concentrations. The fact that EMA labels necrotic cells as well as apoptotic cells before nuclear fragmentation has occurred, together with its photoactivation property, are important characteristics that each contributed to the optimization of this labeling scheme.

This and other automated techniques for scoring in vitro-derived micronuclei will likely benefit screening programs sooner than GLP-compliant tests that are performed to support the registration of new chemicals and pharmaceuticals. Even so, data presented herein suggest that flow cytometry is a platform that could potentially serve both purposes. Additional experience with diverse chemicals, especially those that are cytotoxic but presumably non-genotoxic, will allow for thorough validation of this system.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A kit comprising:
   one or more mammalian cell membrane lysis solutions;
   a first fluorescent DNA dye that permeates dead and dying cells, but not viable cells;
   a second fluorescent DNA dye having a fluorescent emission spectrum which does not substantially overlap with a fluorescent emission spectrum of the first fluorescent DNA dye; and
   an RNase A solution.

2. The kit according to claim 1 wherein the one or more lysis solutions comprises first and second lysis solutions.

3. The kit according to claim 2 wherein the first lysis solution comprises NaCl, Na-Citrate, and tert-Octylphenoxy poly(oxyethylene)ethanol in deionized water.

4. The kit according to claim 2 wherein the second lysis solution comprises citric acid and sucrose in deionized water.

5. The kit according to claim 1 further comprising:
   instructions that describe cell harvest and staining procedures, and also micronucleus scoring via flow cytometry.

6. The kit according to claim 1 further comprising:
   a computer readable storage medium that contains a cytometry data acquisition template for flow cytometric micronucleus scoring.

7. The kit according to claim 1 further comprising:
   a container comprising an in vitro culture of mammalian cells.

8. The kit according to claim 7, wherein the mammalian cells are nucleated cells.

9. A kit comprising:
one or more mammalian cell membrane lysis solutions;
a first fluorescent DNA dye comprising ethidium monoazide;
a second fluorescent DNA dye having a fluorescent emission spectrum which does not substantially overlap with a fluorescent emission spectrum of the first fluorescent DNA dye; and
an RNase A solution.

10. The kit according to claim 9 wherein the one or more lysis solutions comprises first and second lysis solutions.

11. The kit according to claim 10 wherein the first lysis solution comprises NaCl, Na-Citrate, and tert-Octylphenoxy poly(oxyethylene)ethanol in deionized water.

12. The kit according to claim 10 wherein the second lysis solution comprises citric acid and sucrose in deionized water.

13. The kit according to claim 9 wherein the second fluorescent DNA dye is SYTOX Green, YO-PRO-1, SYBR Green I, SYTO11, SYTO12, SYTO13, BOBO-1, YOYO-1, or TOTO-1.

14. The kit according to claim 9 further comprising:
instructions that describe cell harvest and staining procedures, and also micronucleus scoring via flow cytometry.

15. The kit according to claim 9 further comprising:
a computer readable storage medium that contains a cytometry data acquisition template for flow cytometric micronucleus scoring.

16. The kit according to claim 9 further comprising:
a container comprising an in vitro culture of mammalian cells.

17. The kit according to claim 16, wherein the mammalian cells are nucleated cells.

* * * * *